United States Patent
Okamoto et al.

(10) Patent No.: US 11,478,885 B2
(45) Date of Patent: Oct. 25, 2022

(54) METHOD AND APPARATUS OF MANUFACTURING MEDICAL DEVICE

(71) Applicant: Nikkiso Company Limited, Tokyo (JP)

(72) Inventors: Shingo Okamoto, Shizuoka (JP);
Hiroyuki Kawajiri, Shizuoka (JP);
Kosei Nishida, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 0 days.

(21) Appl. No.: 17/128,705

(22) Filed: Dec. 21, 2020

(65) Prior Publication Data

US 2021/0107100 A1    Apr. 15, 2021

Related U.S. Application Data

(63) Continuation of application No. PCT/JP2019/024656, filed on Jun. 21, 2019.

(30) Foreign Application Priority Data

Jun. 22, 2018  (JP) .............................. JP2018-119263

(51) Int. Cl.
*B23P 19/04*        (2006.01)
*A61M 1/36*         (2006.01)
(Continued)

(52) U.S. Cl.
CPC ........... *B23P 19/04* (2013.01); *A61M 1/3639* (2013.01); *A61M 1/3641* (2014.02); *G01L 7/082* (2013.01);
(Continued)

(58) Field of Classification Search
CPC .............. A61M 1/3639; A61M 1/3641; A61M 2207/00–10; G01L 7/022; G01L 7/08;
(Continued)

(56) References Cited

U.S. PATENT DOCUMENTS 4,801,125 A    1/1989 Kocher
4,908,493 A *  3/1990 Susemihl ............... B23K 26/06
                                              219/121.67
(Continued)

FOREIGN PATENT DOCUMENTS

DE    102008034920 A1    9/2009
EP       0074733 A1      3/1983
(Continued)

OTHER PUBLICATIONS

Translation of JP2014204779 (Year: 2014).*
(Continued)

*Primary Examiner* — Matthew P Travers
(74) *Attorney, Agent, or Firm* — Young Basile Hanlon & MacFarlane, P.C.

(57) ABSTRACT

A method of manufacturing a medical device including a case having a first and a second case portion mated together. The case having a space inside and an elastic membrane attached to the case. A first housing space covered by the first case portion and a second housing space covered by the second case portion. Fixing parts at peripheries of the first and the second case portions and at which the first and the second case portions are mated. Holding surfaces at the peripheries of the first and the second case portions. A sealing part at the periphery of the first or the second ease portions with respect to the fixing parts and that seals an entirety of the peripheral edge of the elastic membrane. Forming an air gap between the sealing part and the fixing parts by depressurization or heating the fixing parts that connect the case portions.

18 Claims, 14 Drawing Sheets

(51) Int. Cl.
  G01L 7/08 (2006.01)
  G01L 19/14 (2006.01)
  *A61M 60/109* (2021.01)
  *A61M 60/37* (2021.01)
(52) U.S. Cl.
  CPC .......... *A61M 60/109* (2021.01); *A61M 60/37* (2021.01); *A61M 2207/00* (2013.01); *A61M 2207/10* (2013.01); *G01L 19/143* (2013.01)
(58) Field of Classification Search
  CPC ... G01L 7/082; G01L 19/0023; G01L 19/143; B23P 19/04; B29C 65/08–088
  See application file for complete search history.

(56) References Cited

U.S. PATENT DOCUMENTS

| | | | |
|---|---|---|---|
| 5,221,271 A | 6/1993 | Nicholson et al. | |
| 5,722,946 A | 3/1998 | Mudloff et al. | |
| 6,392,208 B1* | 5/2002 | Arx | B29C 65/02 219/544 |
| 8,092,414 B2 | 1/2012 | Schnell et al. | |
| 8,960,010 B1 | 2/2015 | Crnkovich et al. | |
| 10,775,252 B2 | 9/2020 | Funamura et al. | |
| 2003/0115965 A1 | 6/2003 | Mittelstein et al. | |
| 2004/0050168 A1 | 3/2004 | Uberreiter | |
| 2007/0118153 A1 | 5/2007 | Funamura et al. | |
| 2007/0295093 A1 | 12/2007 | Reiter et al. | |
| 2009/0071258 A1* | 3/2009 | Kouda | A61M 1/3641 73/723 |
| 2010/0018317 A1 | 1/2010 | Kitani et al. | |
| 2010/0186518 A1 | 7/2010 | Jonsson et al. | |
| 2011/0290352 A1 | 12/2011 | Reiter et al. | |
| 2015/0306299 A1 | 10/2015 | Stuva et al. | |
| 2016/0089484 A1 | 3/2016 | Lindley et al. | |
| 2017/0312412 A1 | 11/2017 | Mochizuki | |
| 2017/0340798 A1 | 11/2017 | Lindley et al. | |
| 2020/0198459 A1* | 6/2020 | Bouffier | B29C 65/7814 |

FOREIGN PATENT DOCUMENTS

| | | |
|---|---|---|
| EP | 0330891 A1 | 9/1989 |
| EP | 1843140 A2 | 10/2007 |
| EP | 2155287 A1 | 2/2010 |
| EP | 2155287 B1 | 10/2017 |
| JP | S62-051630 B2 | 10/1987 |
| JP | H02-001275 A | 1/1990 |
| JP | H09-024026 A | 1/1997 |
| JP | 2008-051663 A | 3/2008 |
| JP | 2008-136673 A | 6/2008 |
| JP | 2010-172739 A | 8/2010 |
| JP | 2014-204779 A | 10/2014 |
| JP | 2015-112223 A | 6/2015 |
| JP | 2016-221028 A | 12/2016 |
| JP | 2017-106812 A | 6/2017 |
| JP | 2019-063439 A | 4/2019 |
| WO | 2007/040223 A1 | 4/2007 |
| WO | 2007/120812 A2 | 10/2007 |
| WO | 2008/106191 A2 | 9/2008 |
| WO | 2014/028103 A1 | 2/2014 |
| WO | 2014/093846 A1 | 6/2014 |
| WO | 2015/099932 A1 | 7/2015 |
| WO | 2017/015322 A1 | 1/2017 |
| WO | 2019221202 A1 | 11/2019 |
| WO | 2019221203 A1 | 11/2019 |
| WO | 2019221204 A1 | 11/2019 |
| WO | 2019221205 A1 | 11/2019 |

OTHER PUBLICATIONS

Potentially related U.S. Appl. No. 17/128,668, filed Dec. 21, 2020 entitled "Medical Device and Method of Manufacturing the Same".
International Search Report dated Jun. 11, 2019 for Application No. PCT/JP2019/019393 published as WO2019221202.
Potentially related U.S. Appl. No. 17/093,821, filed Nov. 10, 2020 entitled "Pressure Detector," Published as WO2019221203.
Potentially related U.S. Appl. No. 17/093,823, filed Nov. 10, 2020 entitled "Pressure Detector," Published as WO2019221204.
Potentially related U.S. Appl. No. 17/093,825, filed Nov. 10, 2020 entitled "Pressure Detector," Published as WO2019221205.
Potentially related U.S. Appl. No. 17/093,817, filed Nov. 10, 2020 entitled "Pressure Detector," Published as WO2019221202.
International Search Report dated Jul. 16, 2019 for Application No. PCT/JP2019/024655 published as WO2019/245017.
Extended European Search Report for Application No. 19822788.6, dated Feb. 28, 2022.

* cited by examiner

[Fig. 1]
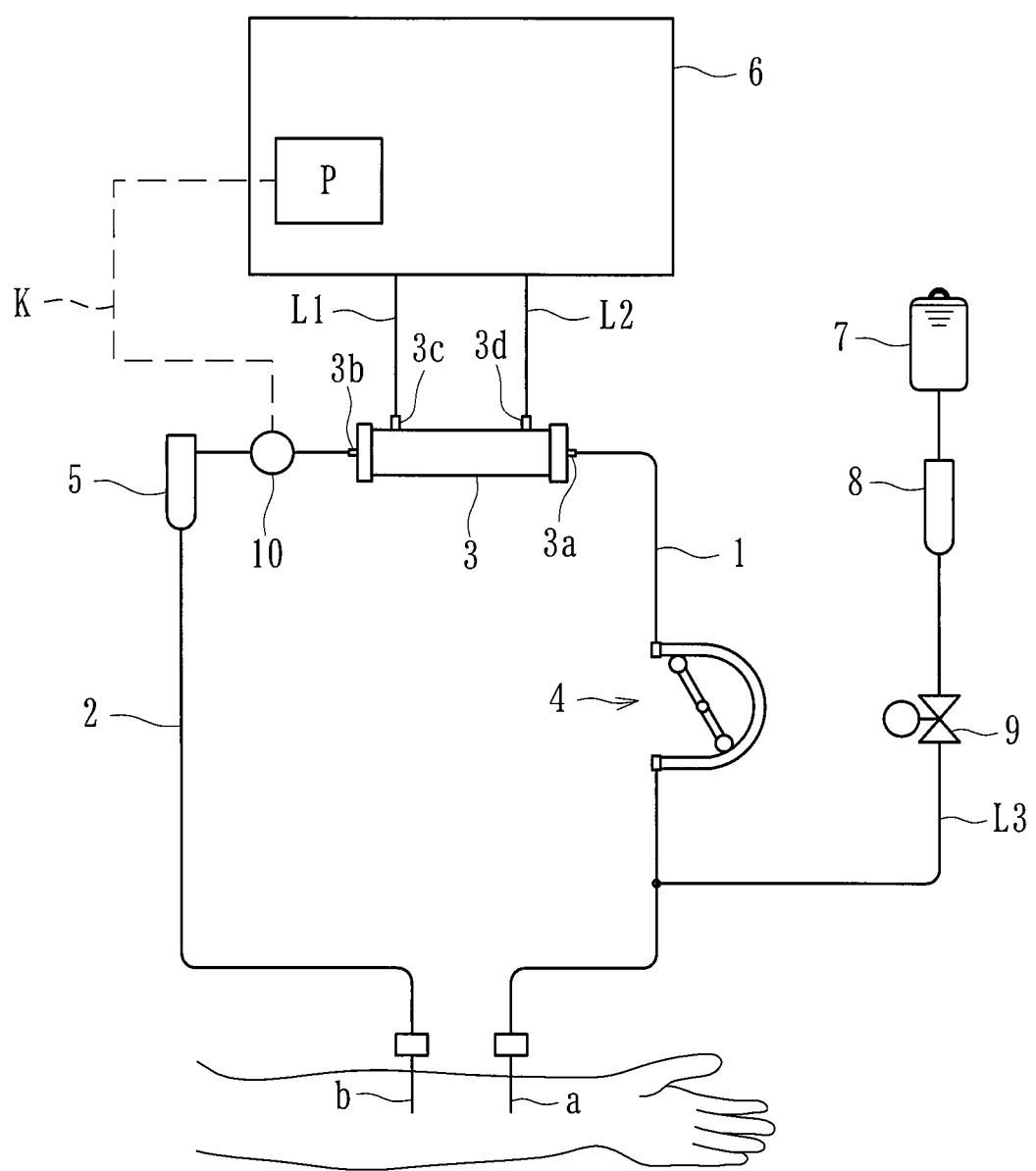

[Fig. 2]
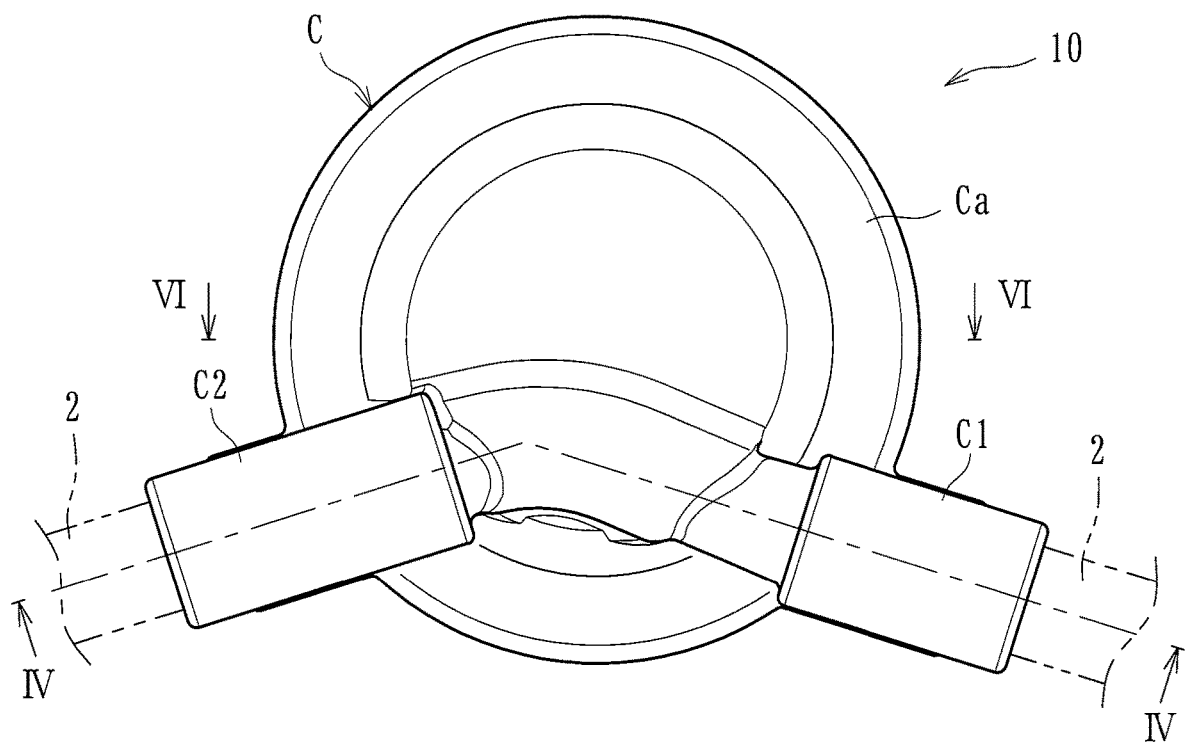
[Fig. 3]
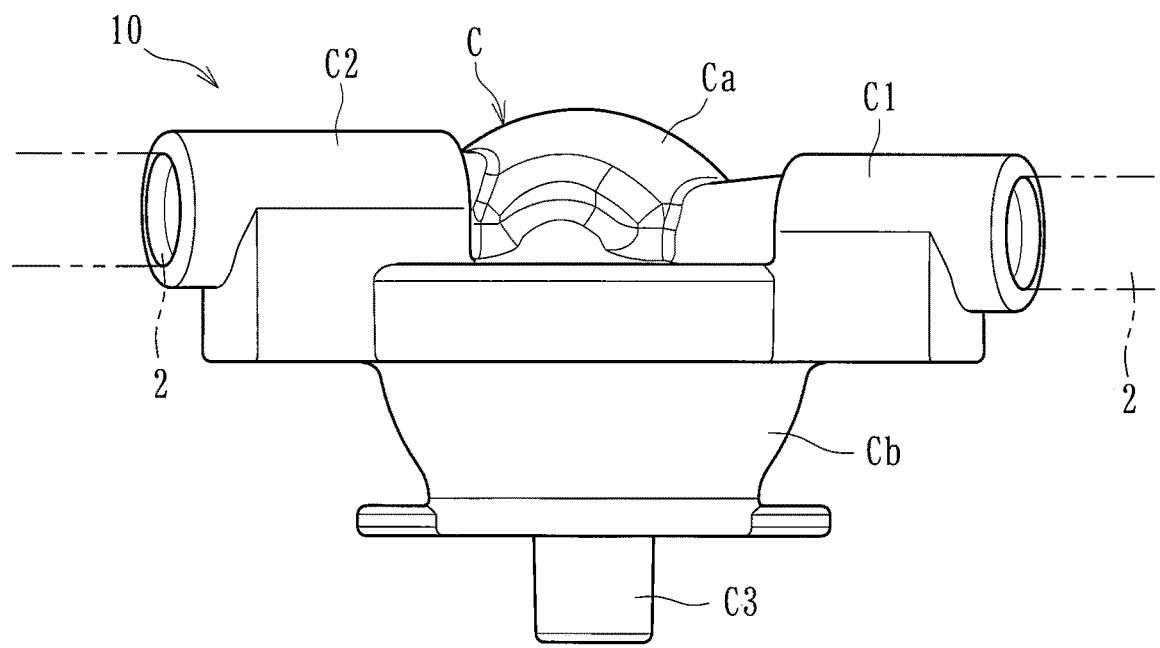

[Fig. 4]
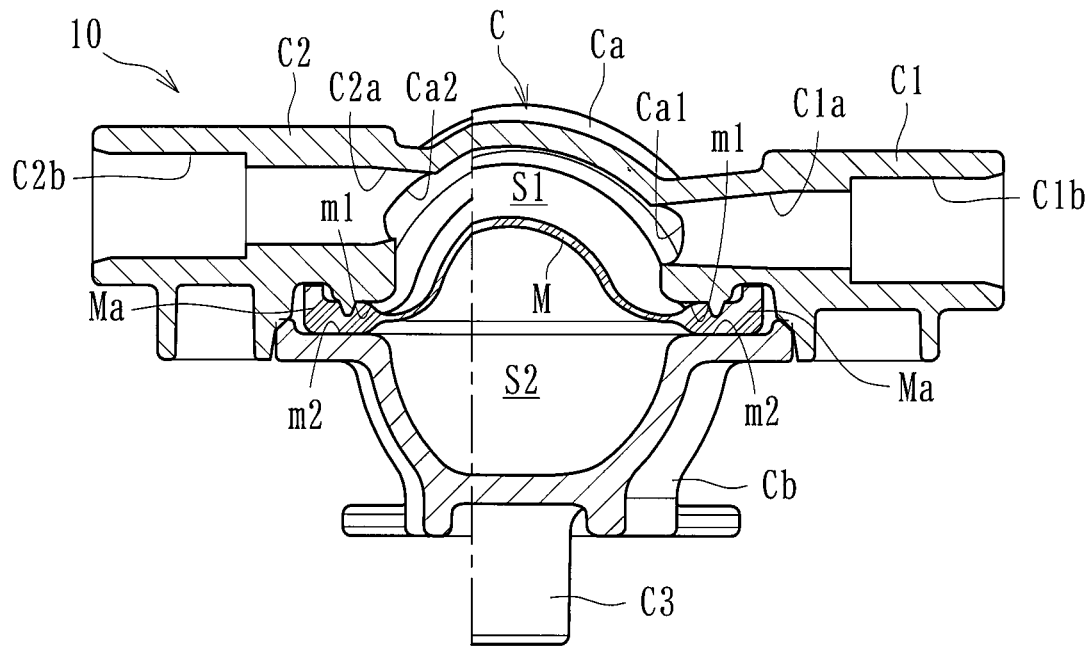
[Fig. 5]
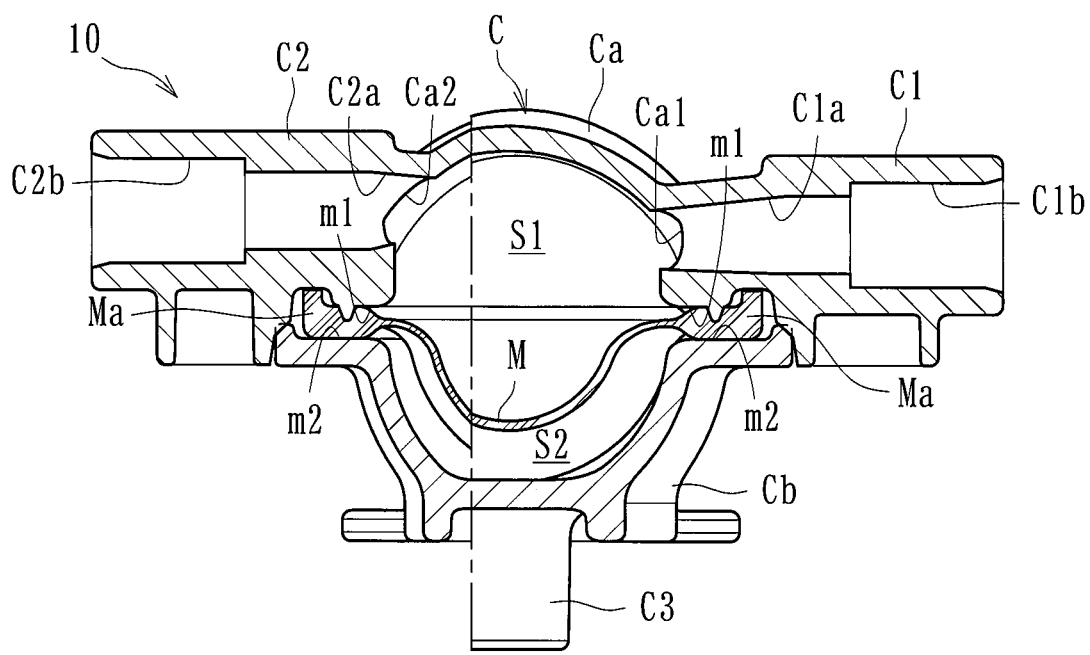

[Fig. 6]
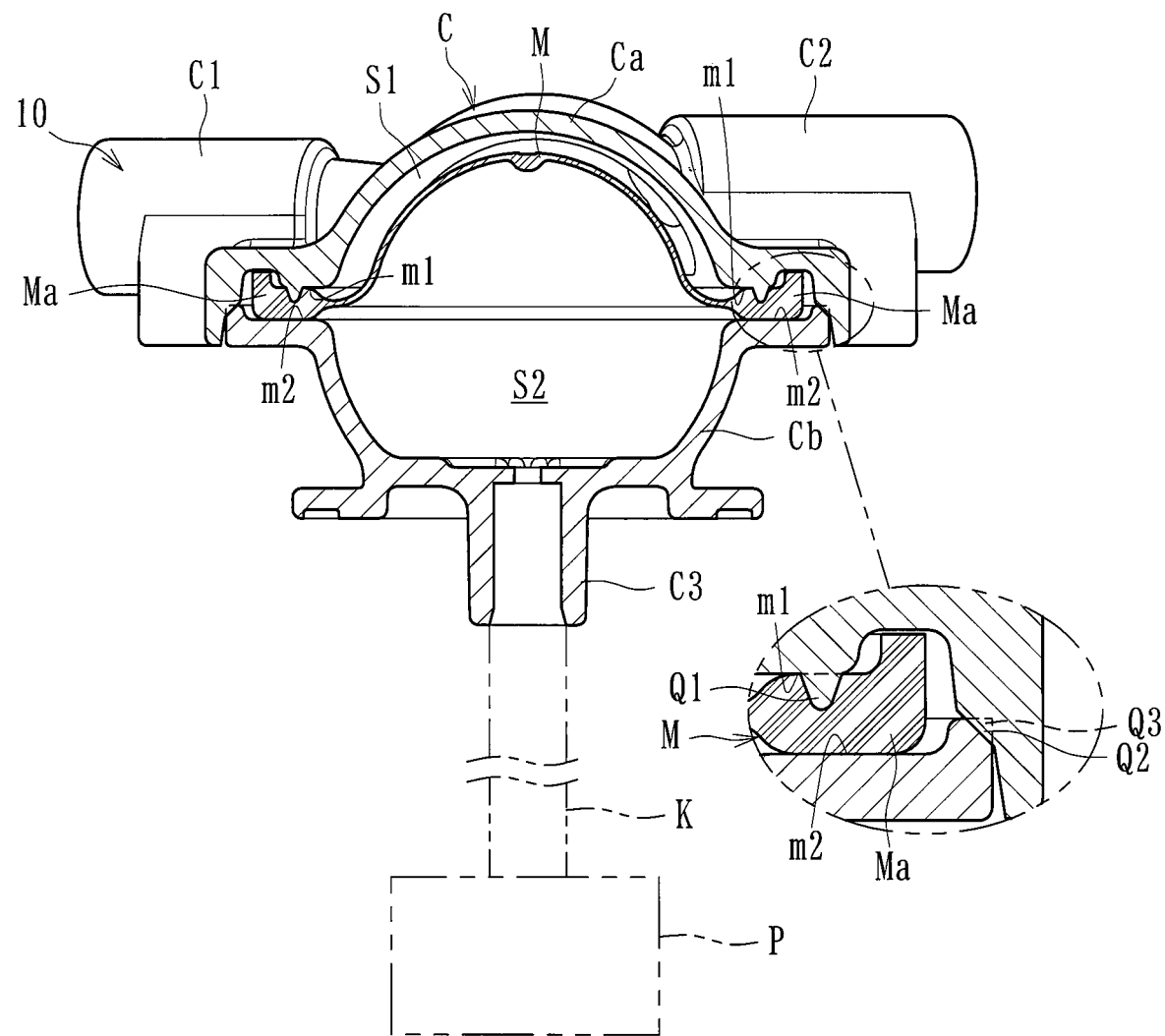

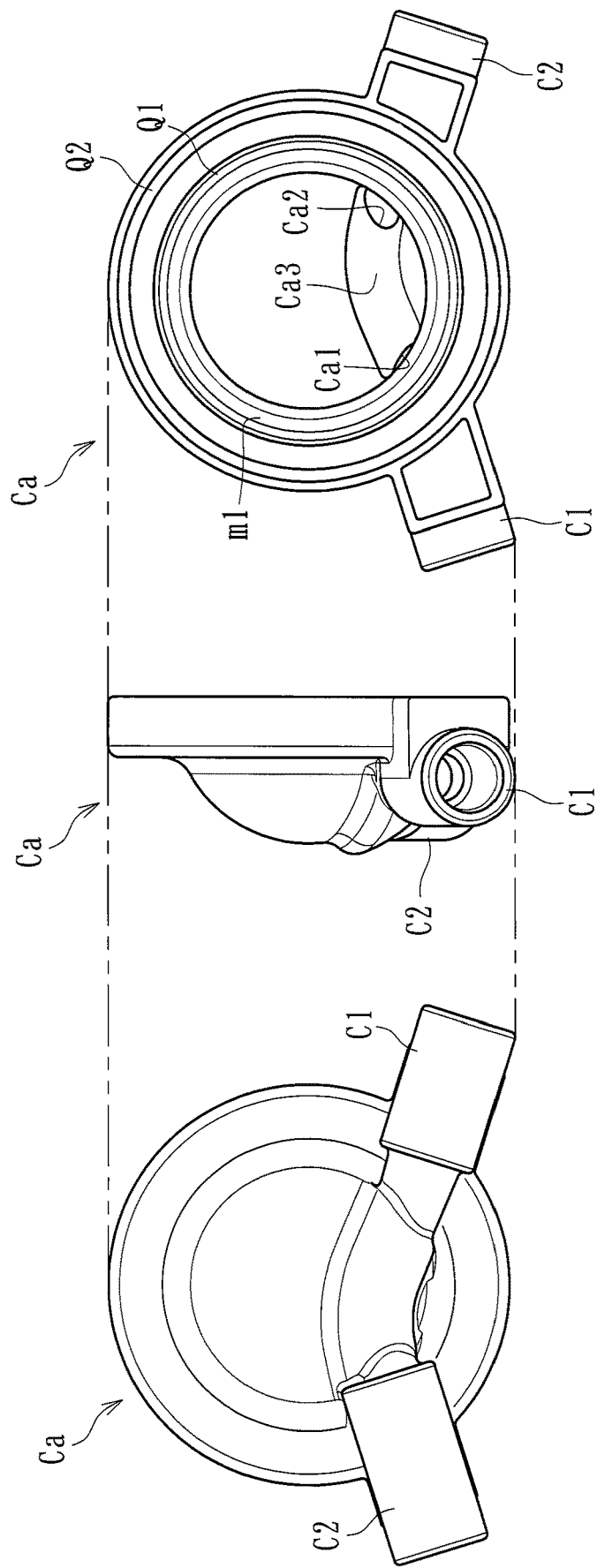
[Fig. 7]

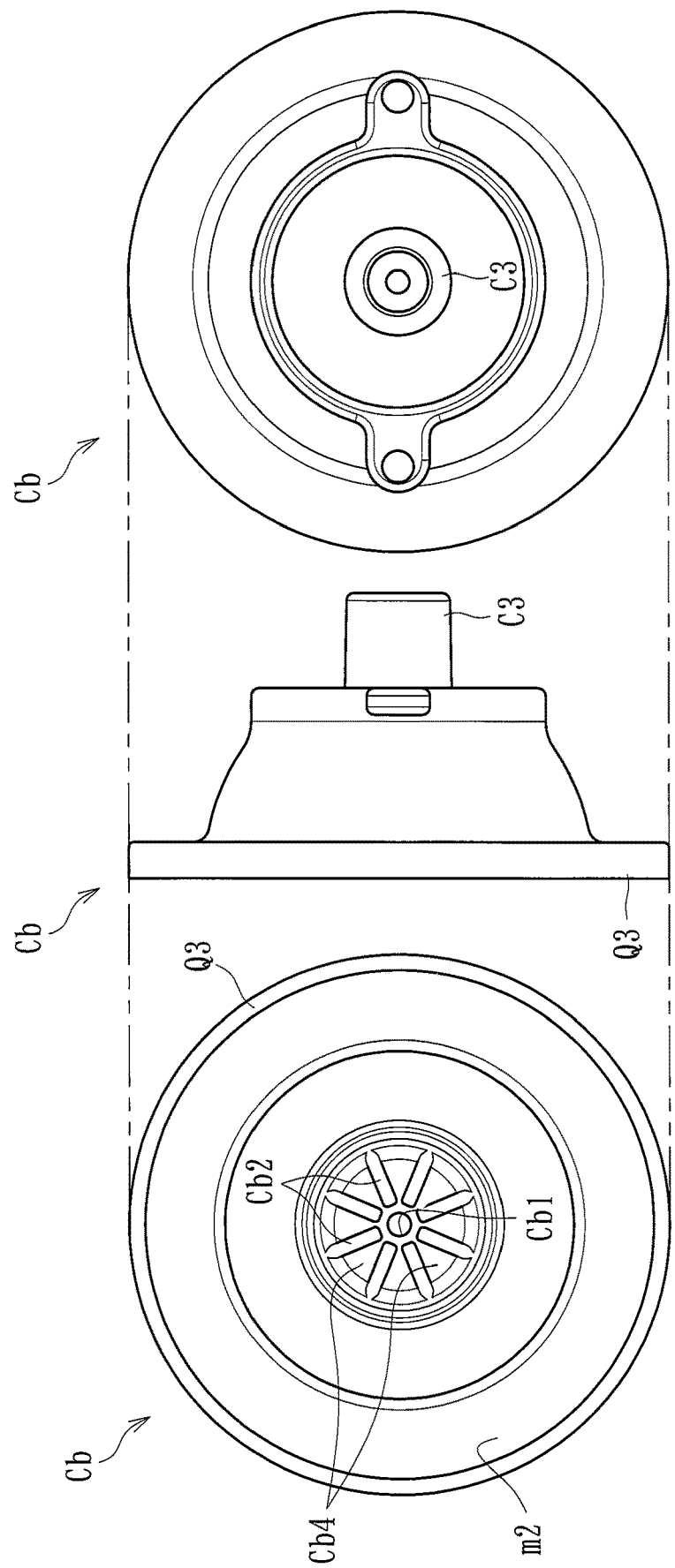
[Fig. 8]

[Fig. 9]
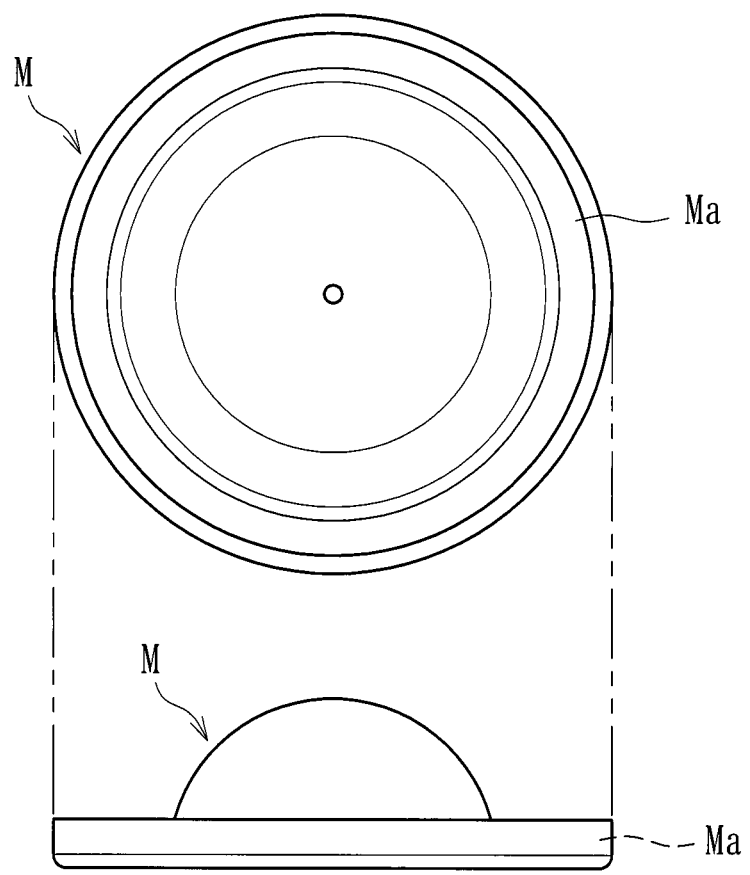

[ Fig. 10 ]
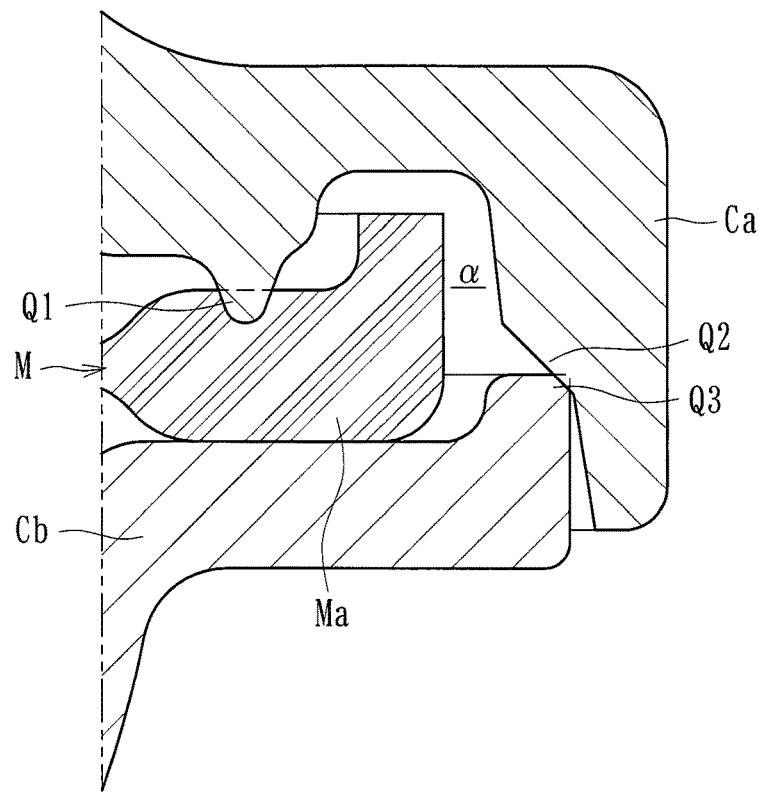
[ Fig. 11 ]
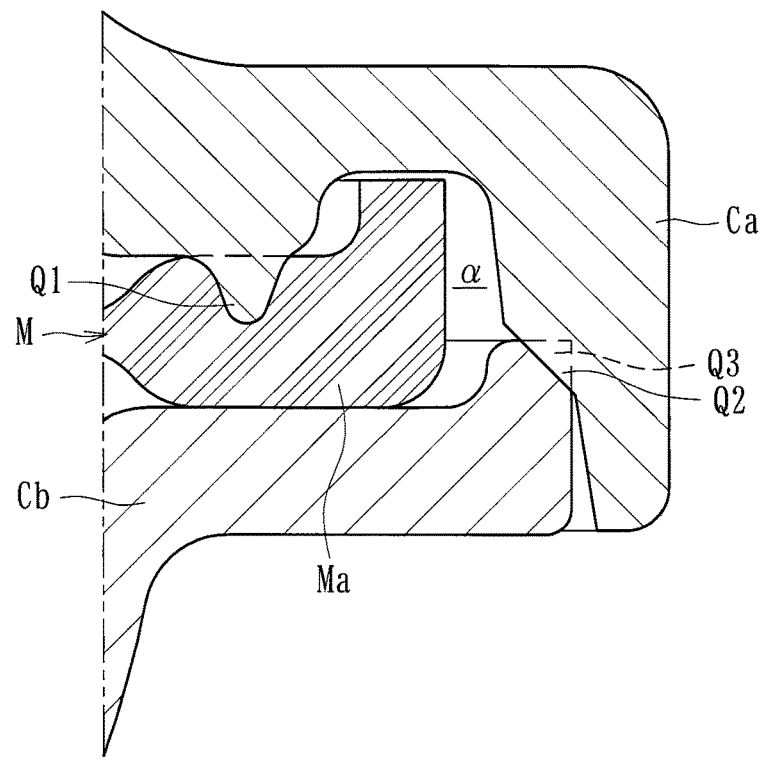

[Fig. 12]
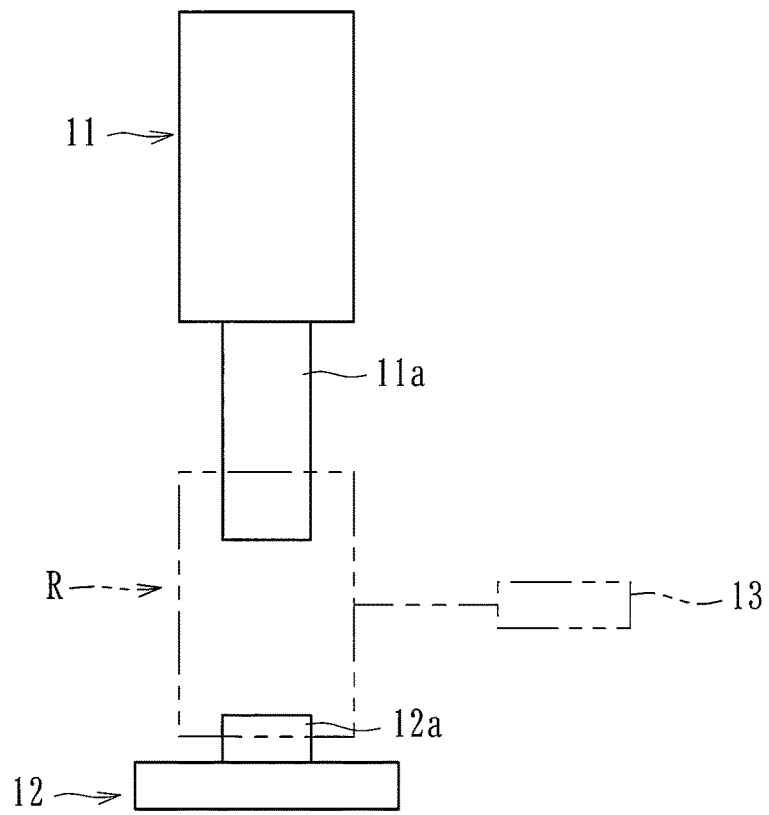
[Fig. 13]
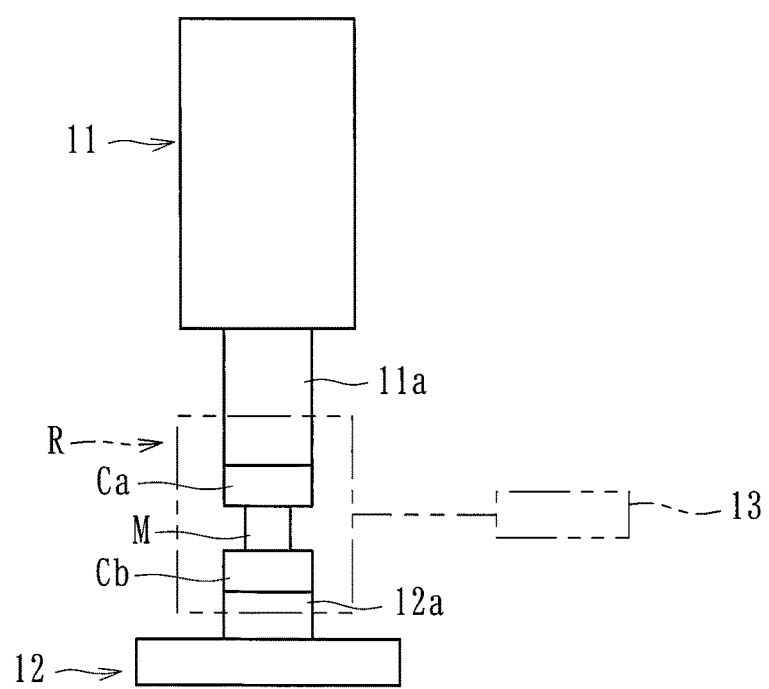

[ Fig. 14 ]
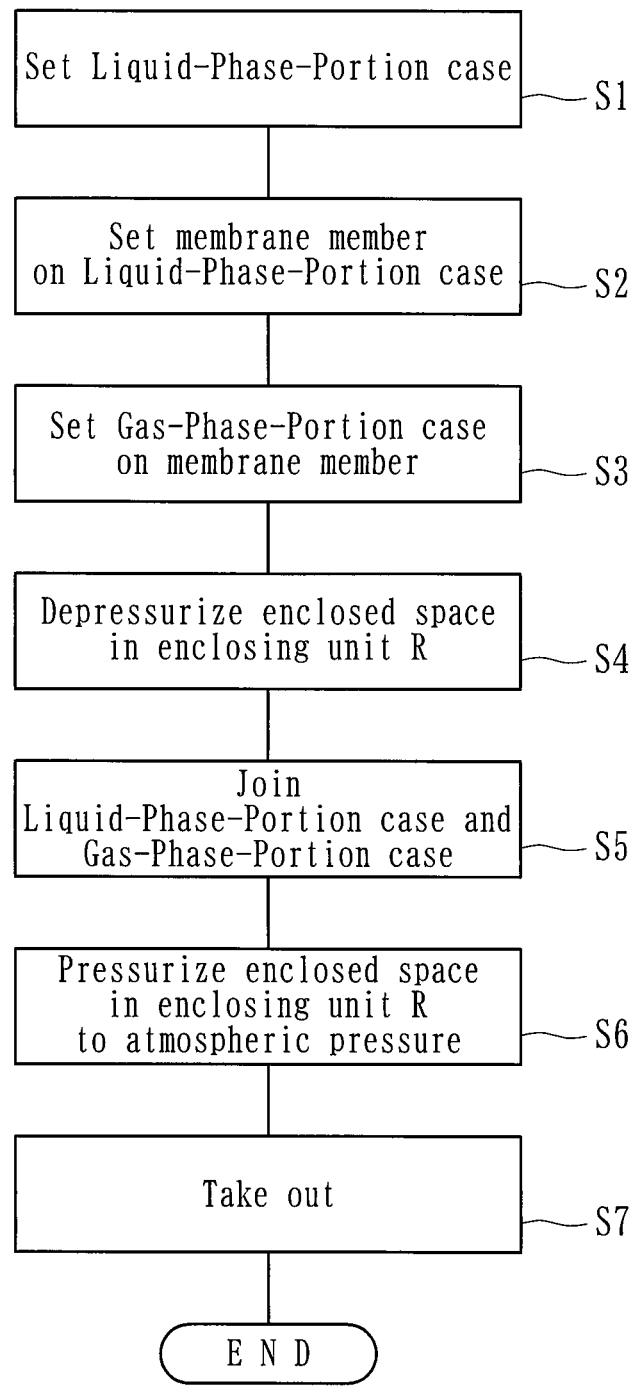

[ Fig. 15 ]
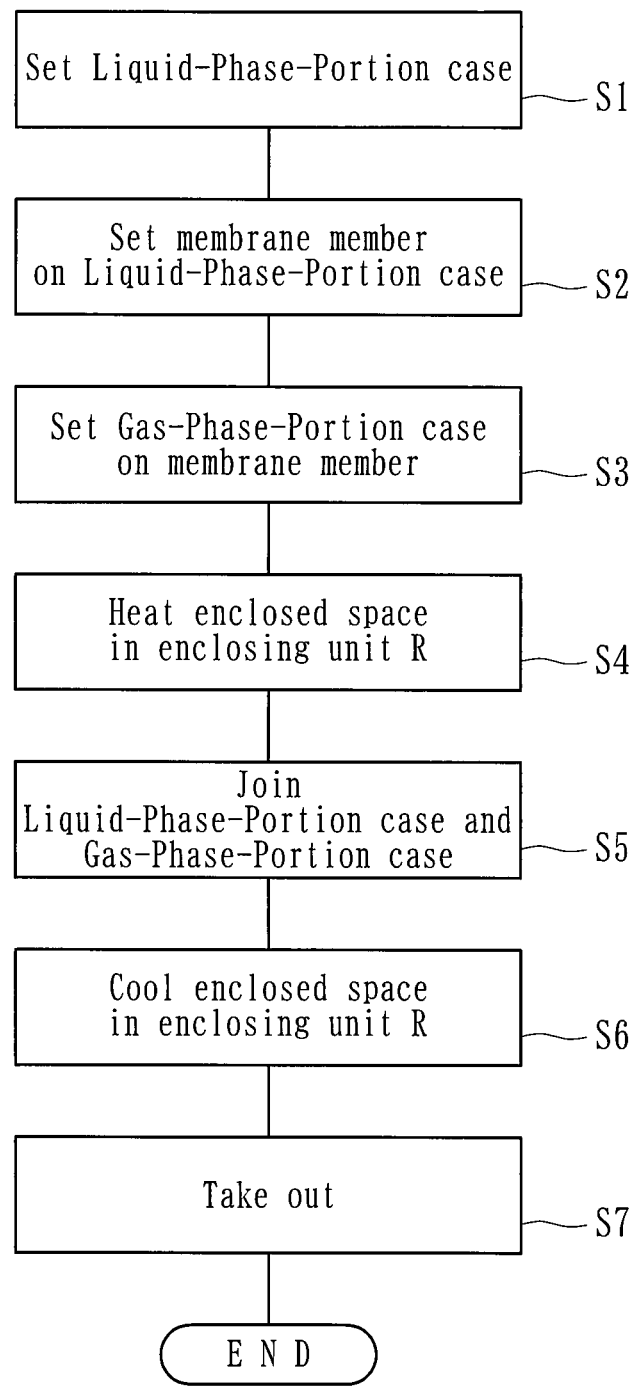

[ Fig. 16 ]
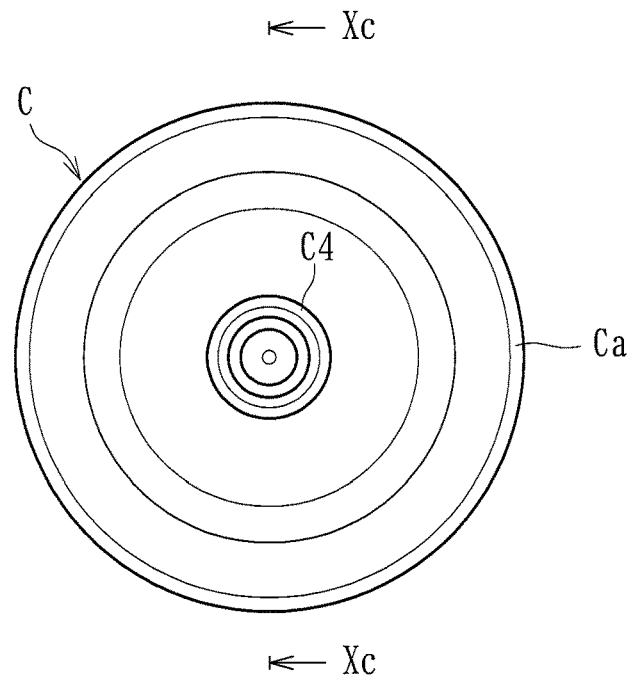
[ Fig. 17 ]
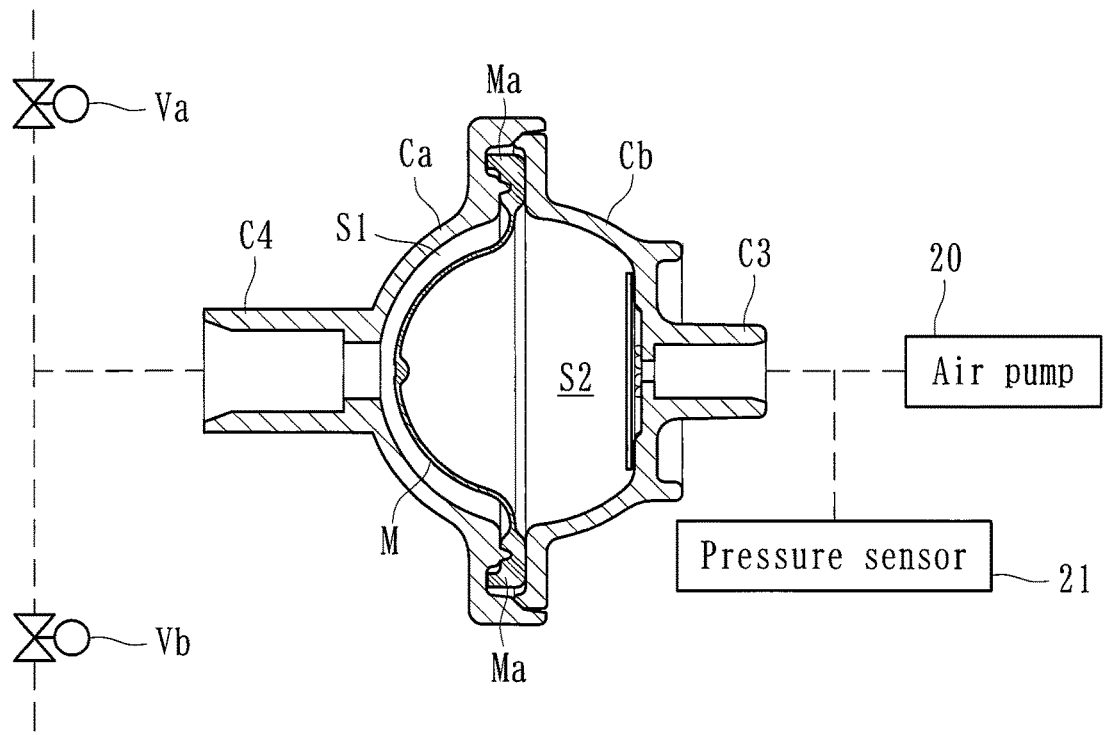

[ Fig. 18 ]
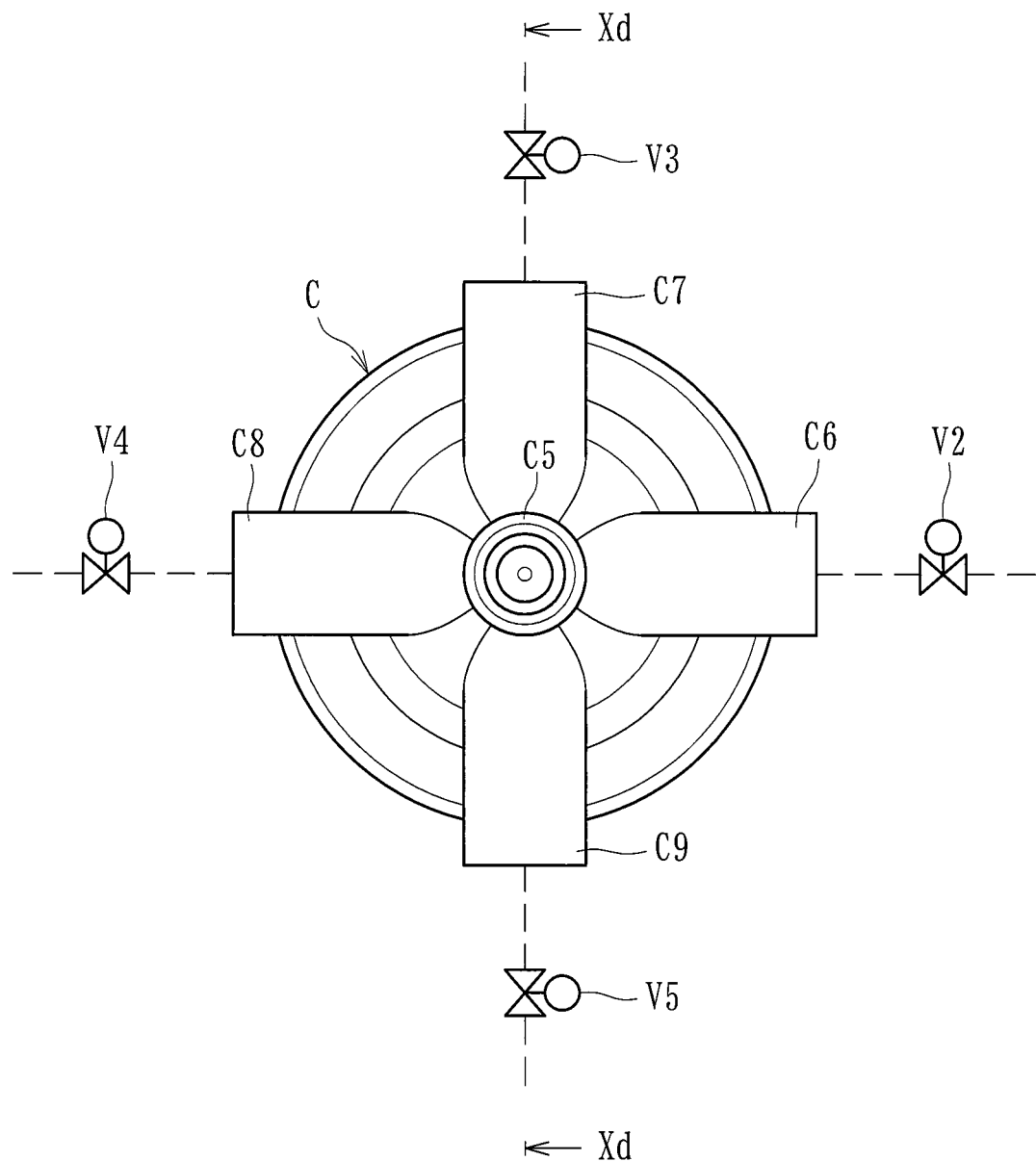

[Fig. 19]
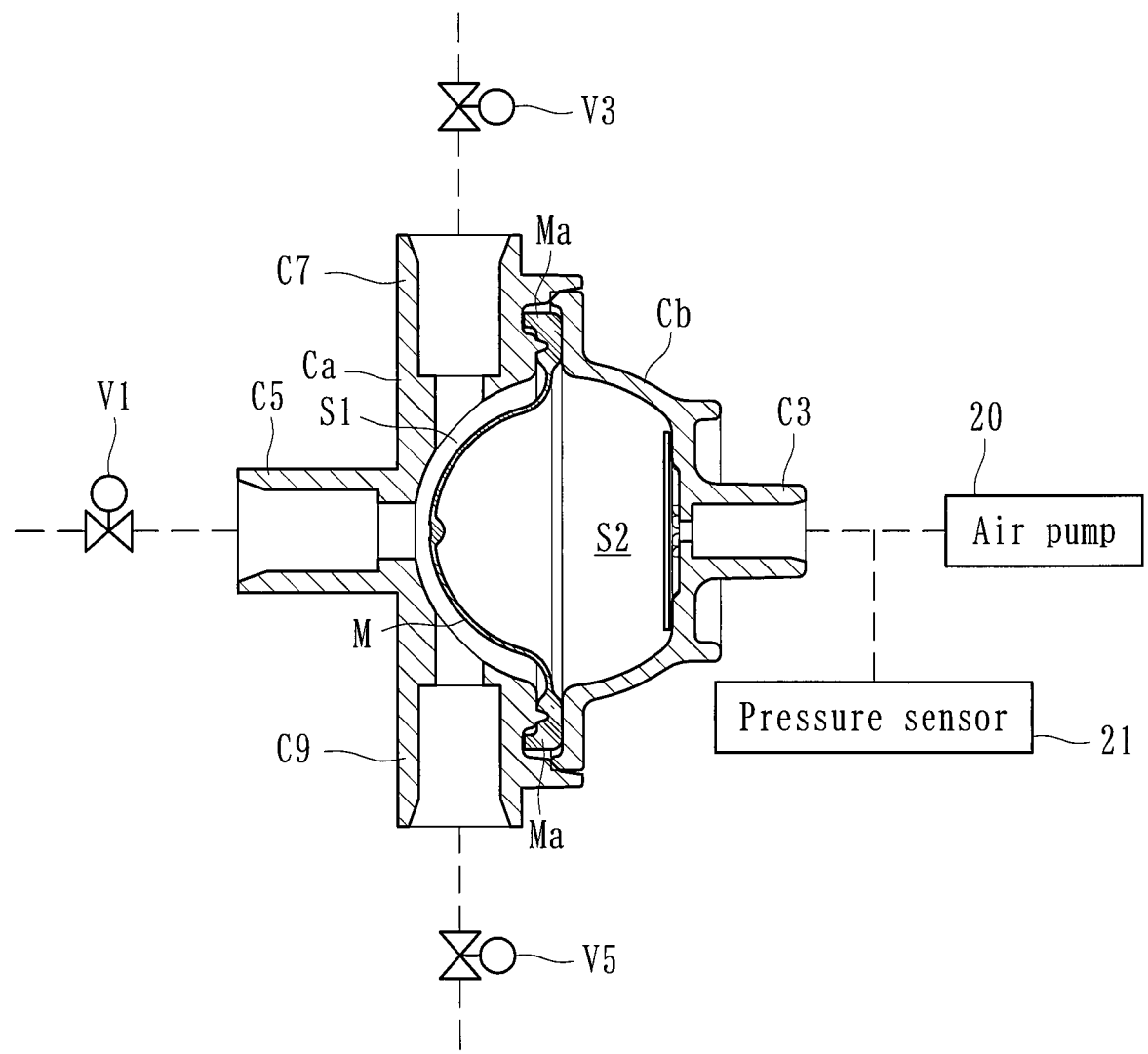

METHOD AND APPARATUS OF MANUFACTURING MEDICAL DEVICE

CROSS-REFERENCE TO RELATED APPLICATION(S)

This application is a continuation of International Application No. PCT/JP2019/024656, filed on Jun. 21, 2019, which claims priority to Japanese Application No. 2018-119263, filed on Jun. 22, 2018, the entire disclosures of which are hereby incorporated by reference.

FIELD

The present invention relates to a method and apparatus of manufacturing a medical device including an elastic membrane with which a first housing space covered by a first case portion and a second housing space covered by a second case portion are separated from each other.

BACKGROUND

In general, dialysis treatment is performed by using a blood circuit for causing blood collected from a patient to extracorporeally circulate and return into the body. Such a blood circuit basically includes, for example, an arterial blood circuit and a venous blood circuit that are connectable to a dialyzer (a blood purifier) including hollow fiber membranes. The arterial blood circuit and the venous blood circuit are provided at distal ends thereof with an arterial puncture needle and a venous puncture needle, respectively. The patient is punctured with the puncture needles, and extracorporeal circulation of blood in the dialysis treatment is thus performed.

To detect the pressure of blood that extracorporeally circulates through a blood circuit, a pressure detector has been proposed as disclosed by PTL 1, for example. The pressure detector includes a case connectable to a blood circuit, and a diaphragm (a membrane member) attached inside the case and with which a liquid-phase portion to be supplied with blood in the blood circuit and a gas-phase portion to be supplied with air are separated from each other, the diaphragm being displaceable in accordance with the pressure of the blood supplied to the liquid-phase portion, the pressure detector being capable of detecting the pressure of the blood by detecting the pressure in the gas-phase portion with a pressure detection sensor. With such a known pressure detector, since the liquid-phase portion and the gas-phase portion are separated from each other by the membrane member, the pressure of the blood in the blood circuit can be detected accurately while the blood is prevented from touching the air in the gas-phase portion.

PTL 1: JP2017-504389 (a Published Japanese Translation of a PCT Application) the teachings of which are expressly incorporated by reference herein for all purposes.

SUMMARY

In the above known pressure detector, when the half-piece cases (the first case portion and the second case portion) are mated to each other and the peripheries thereof are fixed to each other by ultrasonic welding or the like, the entirety of the peripheral edge of the diaphragm is sealed by a sealing part provided on the first case portion or the second case portion. Therefore, a closed space is produced between the sealing part and the fixing part (the welded part). Consequently, in the welding process, the pressure in the closed space may increase excessively.

If the pressure in the closed space increases excessively in a case where the pressure detector as a finished product is subjected to, for example, autoclave sterilization, annealing, or a high-temperature environment of use, the pressure in the closed space further increases to possibly displace the diaphragm in the radial direction and reduce the sealability, resulting in a defective or malfunctioning product. In particular, if press-fitting such as ultrasonic welding is performed in fixing the first case portion and the second case portion to each other, the pressure increase in the closed space is significant, which increases the probability of radial displacement of the diaphragm.

Such a problem is not specific to pressure detectors including diaphragms and also occurs in other medical devices each including an elastic membrane with which housing spaces in a first case portion and a second case portion are separated from each other. The present applicant has decided to thoroughly examine the way of improvements in quality and reliability of such a medical device by suppressing the occurrence of excessive pressure increase in an air gap produced between the sealing part and the fixing part.

The present invention has been conceived in view of the above circumstances and provides a method and apparatus of manufacturing a medical device in which the occurrence of excessive pressure increase in an air gap produced between a sealing part and a fixing part is suppressed for improvements in quality and reliability.

Variation 1 may comprise a method of manufacturing a medical device, the medical device including a case obtained by mating a first case portion and a second case portion to each other, the case having a housing space inside; an elastic membrane as an elastic member attached to the case and with which a first housing space covered by the first case portion and a second housing space covered by the second case portion are separated from each other; fixing parts provided at respective peripheries of the first case portion and the second case portion and at which the first case portion and the second case portion that are mated to each other are fixed to each other; holding surfaces provided at the respective peripheries of the first case portion and the second case portion and between which a peripheral edge of the elastic membrane is held; and a sealing part provided at the periphery of the first case portion or the second case portion on an inner side with respect to the fixing parts and that seals an entirety of the peripheral edge of the elastic membrane held between the holding surfaces. When fixing at the fixing parts and sealing by the sealing part are performed to assemble the first case portion and the second case portion together, an air gap produced between the sealing part and the fixing parts is depressurized or heated.

Variation 2 may comprise the method of manufacturing a medical device according to variation 1, the first case portion and the second case portion that are mated to each other with the elastic membrane interposed in between are secured to a jig; the fixing at the fixing parts and the sealing by the sealing part are performed to assemble the first case portion and the second case portion together; at least the first case portion and the second case portion that are secured to the jig are hermetically enclosed in an enclosed space; and the enclosed space is depressurized or heated.

Variation 3 may comprise the method of manufacturing a medical device according to variation 2, after the enclosed space is depressurized or heated, the enclosed space is pressurized or cooled.

Variation 4 may comprise the method of manufacturing a medical device according to variations 1 to 3, the case is connectable to a flow route for liquid; the first housing space serves as a liquid-phase portion to be supplied with the liquid in the flow route; the second housing space serves as a gas-phase portion to be supplied with gas; the elastic membrane is a membrane member with which the liquid-phase portion and the gas-phase portion are separated from each other and that is displaceable in accordance with a pressure of the liquid supplied into the liquid-phase portion; and the medical device serves as a pressure detector that detects the pressure of the liquid in the flow route by detecting a pressure in the gas-phase portion.

Variation 5 may comprise an apparatus of manufacturing a medical device, the medical device including a case obtained by mating a first case portion and a second case portion to each other, the case having a housing space inside; an elastic membrane as an elastic member attached to the case and with which a first housing space covered by the first case portion and a second housing space covered by the second case portion are separated from each other; fixing parts provided at respective peripheries of the first case portion and the second case portion and at which the first case portion and the second case portion that are mated to each other are fixed to each other; holding surfaces provided at the respective peripheries of the first case portion and the second case portion and between which a peripheral edge of the elastic membrane is held; and a sealing part provided at the periphery of the first case portion or the second case portion on an inner side with respect to the fixing parts and that seals an entirety of the peripheral edge of the elastic membrane held between the holding surfaces. The apparatus includes a depressurizing unit or a heating unit. When fixing at the fixing parts and sealing by the sealing part are performed to assemble the first case portion and the second case portion together, the depressurizing unit or the heating unit depressurizes or heats an air gap produced between the sealing part and the fixing parts.

Variation 6 may comprise the apparatus of manufacturing a medical device according to variation 5 further includes a jig to which the first case portion and the second case portion that are mated to each other with the elastic membrane interposed in between are secured; and an enclosing unit that hermetically encloses at least the first case portion and the second case portion that are secured to the jig in an enclosed space. When the fixing at the fixing parts and the sealing by the sealing part are performed to assemble the first case portion and the second case portion together, the depressurizing unit or the heating unit depressurizes or heats a hermetically enclosed space produced in the enclosing unit.

Variation 7 may comprise the apparatus of manufacturing a medical device according to variation 6, after the enclosed space is depressurized or heated, the enclosed space is pressurized or cooled.

Variation 8 may comprise the apparatus of manufacturing a medical device according to variations 5 to 7, the case is connectable to a flow route for liquid; the first housing space serves as a liquid-phase portion to be supplied with the liquid in the flow route; the second housing space serves as a gas-phase portion to be supplied with gas; the elastic membrane is a membrane member with which the liquid-phase portion and the gas-phase portion are separated from each other and that is displaceable in accordance with a pressure of the liquid supplied into the liquid-phase portion; and the medical device serves as a pressure detector that detects the pressure of the liquid in the flow route by detecting a pressure in the gas-phase portion.

According to each of variations 1 and 5, when the fixing at the fixing parts and the sealing by the sealing part are performed to assemble the first case portion and the second case portion together, the air gap produced between the sealing part and the fixing parts is depressurized or heated. Therefore, the occurrence of excessive pressure increase in the air gap produced between the sealing part and the fixing parts can be suppressed. Consequently, improvements in quality and reliability can be achieved.

According to each of variations 2 and 6, the first case portion and the second case portion that are mated to each other with the elastic membrane interposed in between are secured to the jig; the fixing at the fixing parts and the sealing by the sealing part are performed to assemble the first case portion and the second case portion together; at least the first case portion and the second case portion that are secured to the jig are hermetically enclosed in an enclosed space; and the enclosed space is depressurized or heated. Therefore, depressurization or heating of the air gap can be achieved efficiently.

According to each of variations 3 and 7, after the enclosed space is depressurized or heated, the enclosed space is pressurized or cooled. Therefore, the finished product can be taken out after the environment is stabilized. Hence, an improvement in quality can be achieved.

According to each of variations 4 and 8, the case is connectable to the flow route for liquid; the first housing space serves as the liquid-phase portion to be supplied with the liquid in the flow route; the second housing space serves as the gas-phase portion to be supplied with gas; the elastic membrane is the membrane member with which the liquid-phase portion and the gas-phase portion are separated from each other and that is displaceable in accordance with the pressure of the liquid supplied into the liquid-phase portion; and the medical device serves as the pressure detector that detects the pressure of the liquid in the flow route by detecting the pressure in the gas-phase portion. Therefore, the occurrence of excessive pressure increase in the air gap produced between the sealing part and the fixing parts is suppressed. Consequently, the quality and reliability of the pressure detector can be improved.

BRIEF DESCRIPTION OF THE DRAWINGS

FIG. 1 is a schematic diagram of a dialysis apparatus (a blood purification apparatus) to which a pressure detector as a medical device according to a first embodiment of the present invention is applied.

FIG. 2 is a plan view of the pressure detector.

FIG. 3 is a front view of the pressure detector.

FIG. 4 is a sectional view taken along line IV-IV illustrated in FIG. 2 (with a membrane member displaced toward the side of a liquid-phase portion).

FIG. 5 is a sectional view taken along line IV-IV illustrated in FIG. 2 (with the membrane member displaced toward the side of a gas-phase portion).

FIG. 6 is a sectional view taken along line VI-VI illustrated in FIG. 2.

FIG. 7 is a third-angle projection of a first case portion included in the pressure detector.

FIG. 8 is a third-angle projection of a second case portion included in the pressure detector.

FIG. 9 includes a plan view and a front view of the membrane member included in the pressure detector.

FIG. 10 is an enlarged sectional view of the pressure detector and illustrates a state established before fixing at fixing parts and sealing by a sealing part are achieved.

FIG. 11 is an enlarged sectional view of the pressure detector and illustrates a state established after fixing at the fixing parts and sealing by the sealing part are achieved.

FIG. 12 is a schematic diagram of an apparatus of manufacturing the pressure detector.

FIG. 13 is a schematic diagram of the apparatus of manufacturing the pressure detector.

FIG. 14 is a flow chart illustrating a method of manufacturing the pressure detector (in which depressurization is performed).

FIG. 15 is a flow chart illustrating a method of manufacturing the pressure detector (in which heating is performed).

FIG. 16 is a plan view of a diaphragm pump (a pump including a gas-phase-portion case with a single port) as a medical device according to another embodiment of the present invention.

FIG. 17 is a sectional view taken along line Xc-Xc illustrated in FIG. 16.

FIG. 18 is a plan view of a diaphragm pump (a pump including a gas-phase-portion case with five ports) as a medical device according to yet another embodiment of the present invention.

FIG. 19 is a sectional view taken along line Xd-Xd illustrated in FIG. 18.

DETAILED DESCRIPTION

Embodiments of the present invention will now be described specifically with reference to the drawings.

A blood purification apparatus applied to a first embodiment is a dialysis apparatus for giving dialysis treatment and basically includes, as illustrated in FIG. 1, a blood circuit including an arterial blood circuit 1 and a venous blood circuit 2, a dialyzer 3 (a blood purifier) provided between the arterial blood circuit 1 and the venous blood circuit 2 and that purifies blood flowing through the blood circuit, a blood pump 4, an air-trap chamber 5 provided to the venous blood circuit 2, a dialysis device 6 that supplies dialysate to the dialyzer 3 and drains waste liquid from the dialyzer 3, a physiological-saline supply line L3 (a substitution-fluid supply line) that allows physiological saline as a substitution fluid to be supplied to the blood circuit, and a storage unit 7 that stores the physiological saline as the substitution fluid.

The arterial blood circuit 1 is provided with an arterial puncture needle (a) connectable to a distal end thereof through a connector, and the blood pump 4, which is of a peristaltic type, at a halfway position thereof. The venous blood circuit 2 is provided with a venous puncture needle (b) connectable to a distal end thereof through a connector, and the air-trap chamber 5 at a halfway position thereof. The air-trap chamber 5 is capable of trapping bubbles in the liquid and is provided with a filtering net (not illustrated), thereby being capable of trapping, for example, thrombi and the like at the time of blood return. In this specification, a side on which the puncture needle for blood removal (blood collection) is provided is referred to as the "arterial" side, and a side on which the puncture needle for blood return is provided is referred to as the "venous" side. The "arterial" side and the "venous" side are not defined in accordance with which of the artery and the vein is to be the object of puncture.

The blood pump 4, which is a peristaltic pump provided to the arterial blood circuit 1, is capable of undergoing normal rotation and reverse rotation and causing the liquid in the blood circuit to flow in the direction of rotation thereof. Specifically, the arterial blood circuit 1 includes a squeezable tube that is softer and has a larger diameter than other flexible tubes forming the arterial blood circuit 1. The blood pump 4 includes rollers for squeezing the squeezable tube in the direction of liquid delivery. When the blood pump 4 is activated, the rollers rotate and thus squeeze the squeezable tube (a portion of the blood circuit), whereby the liquid in the tube can be made to flow in the direction of rotation (the direction in which the rollers rotate).

When the blood pump 4 is activated to undergo normal rotation (leftward rotation in the drawing) while a patient is punctured with the arterial puncture needle (a) and the venous puncture needle (b), the patient's blood flows through the arterial blood circuit 1 and reaches the dialyzer 3, where the blood is purified. Then, the blood flows through the venous blood circuit 2 while undergoing bubble removal in the air-trap chamber 5 and returns into the patient's body. That is, the patients blood is purified with the dialyzer 3 while being caused to extracorporeally circulate through the blood circuit from the distal end of the arterial blood circuit 1 to the distal end of the venous blood circuit 2. When the blood pump 4 is activated to undergo reverse rotation (rightward rotation in the drawing), the blood in the blood circuit (a portion of the arterial blood circuit 1 that is between the distal end and a position where the blood pump 4 is provided) can be returned to the patient.

The dialyzer 3 has, in a housing thereof, a blood introduction port 3a, a blood delivery port 3b, a dialysate introduction port 3c, and a dialysate delivery port 3d. The blood introduction port 3a is connected to the arterial blood circuit 1. The blood delivery port 3b is connected to the venous blood circuit 2. The dialysate introduction port 3c and the dialysate delivery port 3d are connected to a dialysate introduction line L1 and a dialysate drain line L2, respectively, extending from the dialysis device 6.

The dialyzer 3 houses a plurality of hollow fibers. Spaces inside the respective hollow fibers form flow routes for blood, and spaces between the inner surface of the housing and the outer surfaces of the hollow fibers form flow routes for dialysate. The hollow fibers each have a number of microscopic holes (pores) extending therethrough from the outer surface to the inner surface, thereby forming a hollow fiber membrane. Impurities and the like contained in the blood are allowed to permeate through the hollow fiber membranes into the dialysate.

On the other hand, the dialysis device 6 includes a liquid delivery unit such as a duplex pump provided over the dialysate introduction line L1 and the dialysate drain line L2. A bypass line that bypasses the liquid delivery unit is provided with an ultrafiltration pump for removing water from the patient's blood flowing in the dialyzer 3. One end of the dialysate introduction line L1 is connected to the dialyzer 3 (the dialysate introduction port 3c), and the other end is connected to a dialysate supply device (not illustrated) that prepares a dialysate at a predetermined concentration. One end of the dialysate drain line L2 is connected to the dialyzer 3 (the dialysate delivery port 3d), and the other end is connected to a drainage unit, not illustrated. The dialysate supplied from the dialysate supply device flows through the dialysate introduction line L1 into the dialyzer 3, and further flows through the dialysate drain line L2 into the drainage unit.

The air-trap chamber 5 is provided with an overflow line extending from the top thereof. The overflow line is provided with a clamp unit, such as an electromagnetic valve, at a halfway position thereof. When the clamp unit such as an electromagnetic valve is opened, the liquid (a priming solution or the like) flowing in the blood circuit can be made to overflow through the overflow line.

The physiological-saline supply line L3 (the substitution-fluid supply line) is connected at one end thereof to the arterial blood circuit 1 between the position where the blood pump 4 is provided and the distal end of the arterial blood circuit 1 through a T-shaped pipe or the like. The physiological-saline supply line L3 forms a flow route (such as a flexible tube or the like) through which the physiological saline (the substitution fluid) to substitute for the blood in the blood circuit is allowed to be supplied to the arterial blood circuit 1. The physiological-saline supply line L3 is provided at the other end thereof with the storage unit 7 (a so-called "saline bag"), in which a predetermined amount of physiological saline is stored. The physiological-saline supply line L3 is further provided at a halfway position thereof with an air-trap chamber 8.

The physiological-saline supply line L3 according to the present embodiment is further provided with a clamp unit 9 (such as an electromagnetic valve or the like). The clamp unit 9 is capable of opening and closing the physiological-saline supply line L3, thereby closing and opening the flow route. The state of the physiological-saline supply line L3 is arbitrarily switchable by opening or closing the clamp unit 9, between a closed state where the flow route is closed and an open state where the physiological saline (the substitution fluid) is allowed to flow. The clamp unit 9 may be replaced with a general-purpose device such as a pair of forceps with which the flow route of the physiological-saline supply line L3 can be manually closed and opened.

The blood circuit applied to the present embodiment is provided with a pressure detector 10 as a medical device. The pressure detector 10 is connected to the venous blood circuit 2 at a position between the dialyzer 3 and the air-trap chamber 5 and is capable of detecting the pressure of the blood flowing in the venous blood circuit 2 (the blood circuit). Specifically, as illustrated in FIGS. 2 to 6, the pressure detector 10 includes a case C connectable to the flow route for liquid (in the present embodiment, the venous blood circuit 2 (the blood circuit)), and a membrane member M provided in the case C and with which a liquid-phase portion S1 to be supplied with the liquid in the flow route (in the present embodiment, the blood in the venous blood circuit 2 (the blood circuit)) and a gas-phase portion S2 to be supplied with air are separated from each other, the membrane member M being displaceable in accordance with the pressure of the liquid (blood) supplied to the liquid-phase portion S1. The pressure detector 10 is capable of detecting the pressure of the liquid in the flow route (the venous blood circuit 2) by detecting the pressure in the gas-phase portion S2 with a pressure detection sensor P.

The case C is a hollow molded component obtained by molding a predetermined resin material or the like. The case C is a combination of a liquid-phase-portion case Ca defining the liquid-phase portion S1 and a gas-phase-portion case Cb defining the gas-phase portion S2. Specifically, the case C is obtained by mating the liquid-phase-portion case Ca (a first case portion) and the gas-phase-portion case Cb (a second case portion) to each other and having a housing space inside. The liquid-phase-portion case Ca has an inlet port C1 and an outlet port C2 integrally molded therewith. The inlet port C1 and the outlet port C2 are each connectable to the flow route for liquid and allow the flow route to communicate with the liquid-phase portion S1. The gas-phase-portion case Cb has a connection port C3 integrally molded therewith. The connection port C3 is connectable to one end of a pipe portion K, to be described below, and allows the one end to communicate with the gas-phase portion S2. The functions of the inlet port C1 and the outlet port C2 of introducing and discharging the liquid may be switched therebetween (that is, the liquid may be discharged from the inlet port C1 while being introduced into the outlet port C2).

The liquid-phase-portion case Ca has an annular holding surface m1 (see FIG. 7) at the outer periphery thereof. The gas-phase-portion case Cb has an annular holding surface m2 (see FIG. 8) at the outer periphery thereof. When the liquid-phase-portion case Ca and the gas-phase-portion case Cb are mated to each other into an assembly, a periphery Ma of the membrane member M is placed between the holding surface m1 and the holding surface m2. Thus, the membrane member M can be attached in a sealed manner. A space thus provided in the case C is separated (sectioned) by the membrane member M into the liquid-phase portion S1 and the gas-phase portion S2.

The membrane member M serves as a diaphragm provided in the case C and is made of a flexible material that is displaceable or deformable in conformity with pressure change occurring in the liquid-phase portion S1 or the gas-phase portion S2. The membrane member M according to the present embodiment is an elastic member attached to the case C and with which the liquid-phase portion S1 (a first housing space) covered by the liquid-phase-portion case Ca (the first case portion) and the gas-phase portion S2 (a second housing space) covered by the gas-phase-portion case Cb (the second case portion) are separated from each other. As illustrated in FIG. 9, the periphery Ma of the membrane member M projects laterally so as to be held between the holding surfaces m1 and m2. If the pressure of the liquid (the hydraulic pressure) in the liquid-phase portion S1 is low, as illustrated in FIG. 4, the membrane member M is displaced toward the side of the liquid-phase portion S1, whereby the capacity of the gas-phase portion S2 is increased. If the pressure of the liquid (the hydraulic pressure) in the liquid-phase portion S1 is high, as illustrated in FIG. 5, the membrane member M is displaced toward the side of the gas-phase portion S2, whereby the capacity of the gas-phase portion S2 is reduced.

The gas-phase-portion case Cb has an opening Cb1 (see FIG. 8) substantially at the center of the bottom thereof. The opening Cb1 provided in the inner surface (the bottom) of the gas-phase-portion case Cb allows the flow route in the connection port C3 and the gas-phase portion S2 to communicate with each other. Accordingly, air (gas) is allowed to be introduced into or discharged from the gas-phase portion S2 in accordance with the displacement of the membrane member M. The pipe portion K is connected at one end thereof to the connection port C3 and at the other end thereof to the pressure detection sensor P (a pressure-detecting unit). Therefore, as air (gas) is introduced or discharged through the opening Cb1 with the displacement of the membrane member M, the pressure detection sensor P can detect the pressure in the gas-phase portion S2. Note that the connection port C3 is not limited to the one to be connected to the pipe portion K and may be connected to another element capable of transmitting the pressure in the gas-phase portion S2 to the pressure detection sensor P. Furthermore, as illustrated in FIG. 8, the gas-phase portion S2 has a plurality of ribs Cb2 in recesses Cb4 and around the opening Cb1. The ribs Cb2 project radially about the opening Cb1.

The inlet port C1 according to the present embodiment is a portion (a projected portion) connectable to the flow route for liquid (the blood circuit) and includes, as illustrated in FIGS. 4 and 5, a flow-route portion C1a through which the liquid (blood) flows into an inlet opening Ca1 (see FIG. 7)

of the liquid-phase portion S1, and a connecting portion C1*b* connectable to the flow route (the blood circuit). Specifically, the flow-route portion C1*a* and the connecting portion C1*b* are continuous with each other in the axial direction thereof in the projected portion forming the inlet port C1. When a tube forming the flow route is connected to the connecting portion C1*b*, the liquid in the flow route can be made to flow into the flow-route portion C1*a* and then into the liquid-phase portion S1 through the inlet opening Ca1. Note that the inlet port C1 may be shaped as a recess to which the tube forming the flow route is to be connected.

The outlet port C2 according to the present embodiment is a portion (a projected portion) connectable to the flow route for liquid (the blood circuit) and includes, as illustrated in the drawings, a flow-route portion C2*a* through which the liquid (blood) having flowed into the liquid-phase portion S1 is discharged from an outlet opening Ca2 (see FIG. 7), and a connecting portion C2*b* connectable to the flow route (the blood circuit). Specifically, the flow-route portion C2*a* and the connecting portion C2*b* are continuous with each other in the axial direction thereof in the projected portion forming the outlet port C2. When a tube forming the flow route is connected to the connecting portion C2*b*, the liquid having flowed into the liquid-phase portion S1 can be made to flow into the flow-route portion C2*a* and then to be discharged to a flow route (the blood circuit) on the downstream side. Note that the outlet port C2 may be shaped as a recess to which the tube forming the flow route is to be connected.

As illustrated in FIGS. 10 and 11, the liquid-phase-portion case Ca (the first case portion) and the gas-phase-portion case Cb (the second case portion) have fixing parts Q2 and Q3 at the respective peripheries thereof. Furthermore, the liquid-phase-portion case Ca has a sealing part Q1 at the periphery thereof on the inner side with respect to the fixing parts Q2 and Q3 (on the inner side of the liquid-phase-portion case Ca and the gas-phase-portion case Cb). In the present embodiment, the sealing part Q1 is provided only at the periphery of the liquid-phase-portion case Ca. Alternatively, the sealing part Q1 may be provided only at the periphery of the gas-phase-portion case Cb on the inner side with respect to the fixing parts Q2 and Q3, or at each of the peripheries of the liquid-phase-portion case Ca and the gas-phase-portion case Cb on the inner side with respect to the fixing parts Q2 and Q3.

The fixing parts Q2 and Q3 are provided at the respective peripheries of the liquid-phase-portion case Ca and the gas-phase-portion case Cb and for fixing the liquid-phase-portion case Ca and the gas-phase-portion case Cb to each other in a state where the two are mated to each other. In the present embodiment, as illustrated in FIG. 10, when the liquid-phase-portion case Ca and the gas-phase-portion case Cb are mated to each other, the fixing parts Q2 and Q3 come into contact with each other. Furthermore, as illustrated in FIG. 11, when an ultrasonic wave is applied to the liquid-phase-portion case Ca and the gas-phase-portion case Cb that are pressed against each other, the fixing parts Q2 and Q3 melt, whereby the liquid-phase-portion case Ca and the gas-phase-portion case Cb are welded to each other. In other words, the liquid-phase-portion case Ca and the gas-phase-portion case Cb according to the present embodiment are press-bonded to each other by ultrasonic welding and are thus fixed (welded) to each other, whereby a housing space (including the liquid-phase portion S1 and the gas-phase portion S2) is provided thereinside.

The sealing part Q1 is provided at the periphery of the liquid-phase-portion case Ca or the gas-phase-portion case Cb on the inner side with respect to the fixing parts Q2 and Q3 and seals the entirety of the peripheral edge of the membrane member M held between the holding surfaces m1 and m2. In the present embodiment, as illustrated in FIG. 10, the sealing part Q1 is a ridge projecting from the holding surface m1 of the liquid-phase-portion case Ca toward the holding surface m2 of the gas-phase-portion case Cb. As illustrated in FIG. 11, in the process of melting the fixing parts Q1 and Q2 and fixing the two to each other by applying an ultrasonic wave to the liquid-phase-portion case Ca and the gas-phase-portion case Cb that are pressed against each other, the sealing part Q1 compresses the periphery Ma of the membrane member M in the thicknesswise direction and thus seals the periphery Ma.

When the liquid-phase-portion case Ca and the gas-phase-portion case Cb are fixed to each other by melting the fixing parts Q2 and Q3 and the sealing by the sealing part Q1 is thus achieved, an air gap ($\alpha$) is produced between the sealing part Q1 and the fixing parts Q2 and Q3. The air gap ($\alpha$) is a space produced in the process of bringing the liquid-phase-portion case Ca and the gas-phase-portion case Cb into contact with each other so as to be welded to each other. The air gap ($\alpha$) is sealed by the sealing part Q1. Therefore, if neither depressurization nor heating according to the present embodiment is performed, the pressure thereinside may increase excessively.

Now, an apparatus of manufacturing the pressure detector as a medical device according to the present embodiment will be described.

As illustrated in FIGS. 12 and 13, the manufacturing apparatus includes an ultrasonic welding apparatus 11, a jig 12, an enclosing unit R, and a depressurizing unit 13. When the welding (fixing) at the fixing parts (Q2 and Q3) and the sealing by the sealing part Q1 are performed to assemble the liquid-phase-portion case Ca (the first case portion) and the gas-phase-portion case Cb (the second case portion) together, an enclosed space produced in the enclosing unit R is depressurized.

The jig 12 includes a mounting portion 12*a* on which the liquid-phase-portion case Ca (the first case portion) and the gas-phase-portion case Cb (the second case portion) that are mated to each other with the membrane member M interposed in between are mounted and positioned. The jig 12 is set below the ultrasonic welding apparatus 11. The ultrasonic welding apparatus 11 includes a horn 11*a* capable of generating an ultrasonic wave. The ultrasonic welding apparatus 11 is capable of pressing the horn 11*a* against the liquid-phase-portion case Ca (the first case portion) and the gas-phase-portion case Cb (the second case portion) that are secured to the mounting portion 12*a* of the jig 12, thereby applying the ultrasonic wave thereto.

As illustrated in FIGS. 10 and 11, the fixing parts Q2 and Q3 of the liquid-phase-portion case Ca and the gas-phase-portion case Cb against which the horn 11*a* has been pressed by the ultrasonic welding apparatus 11 are pressed against each other and fixed (welded) to each other by the effect of the ultrasonic wave. Furthermore, pressing the horn 11*a* causes the sealing part Q1 to compress the membrane member M, whereby sealing is achieved. Consequently, housing spaces (the liquid-phase portion S1 and the gas-phase portion S2) are produced thereinside.

The enclosing unit R is a container or the like in which a hermetically enclosed space can be produced thereinside. As illustrated in FIG. 13, the enclosing unit R is capable of hermetically enclosing at least the liquid-phase-portion case Ca (the first case portion) and the gas-phase-portion case Cb (the second case portion) that are secured to the jig 12. The enclosing unit R has a door or the like. When the door is open, the liquid-phase-portion case Ca (the first case portion) and the gas-phase-portion case Cb (the second case portion) can be put into or taken out of the enclosing unit R. When the door is closed, a hermetically enclosed space can be produced.

The depressurizing unit 13 is, for example, a blower or the like capable of exhausting the air from the enclosing unit R to the outside and thus reducing the pressure in the enclosing unit R. When the fixing at the fixing parts Q2 and Q3 and the sealing by the sealing part Q1 are performed to assemble the liquid-phase-portion case Ca (the first case portion) and the gas-phase-portion case Cb (the second case portion) together, the depressurizing unit 13 depressurizes the enclosed space produced in the enclosing unit R. Therefore, when the fixing at the fixing parts Q2 and Q3 and the sealing by the sealing part Q1 are performed to assemble the liquid-phase-portion case Ca (the first case portion) and the gas-phase-portion case Cb (the second case portion) together, the air gap ($\alpha$) produced between the sealing part Q1 and the fixing parts Q2 and Q3 can be depressurized.

The depressurizing unit 13 may be replaced with a heating unit 13. The heating unit 13 is, for example, a heater or the like capable of heating the air in the enclosing unit R. When the fixing at the fixing parts Q2 and Q3 and the sealing by the sealing part Q1 are performed to assemble the liquid-phase-portion case Ca (the first case portion) and the gas-phase-portion case Cb (the second case portion) together, the heating unit 13 heats the enclosed space produced in the enclosing unit R. Therefore, when the fixing at the fixing parts Q2 and Q3 and the sealing by the sealing part Q1 are performed to assemble the liquid-phase-portion case Ca (the first case portion) and the gas-phase-portion case Cb (the second case portion) together, the air gap ($\alpha$) produced between the sealing part Q1 and the fixing parts Q2 and Q3 can be heated.

Now, methods of manufacturing the pressure detector as a medical device according to the present embodiment will be described with reference to flow charts illustrated in FIGS. 14 and 15.

First, a method in which depressurization by the depressurizing unit 13 is performed will be described with reference to the flow chart illustrated in FIG. 14. The liquid-phase-portion case Ca is positioned with respect to the jig 12 and is secured to the jig 12 (S1). Subsequently, the membrane member M is set on the secured liquid-phase-portion case Ca (S2). Then, the gas-phase-portion case Cb is set on the membrane member M (S3), whereby the liquid-phase-portion case Ca (the first case portion) and the gas-phase-portion case Cb (the second case portion) are mated to each other with the membrane member M interposed in between.

Subsequently, a hermetically enclosed space is produced in the enclosing unit R, and the depressurizing unit 13 is activated, whereby the enclosed space is depressurized (S4). In the depressurized state, the ultrasonic welding apparatus 11 is activated to press the horn 11a against the liquid-phase-portion case Ca (the first case portion) and the gas-phase-portion case Cb (the second case portion), whereby the fixing parts Q2 and Q3 are pressed against each other and fixed (welded) to each other by the effect of the ultrasonic wave. Furthermore, pressing the horn 11a cases the sealing part Q1 to compress the membrane member M, whereby sealing is achieved. Thus, the liquid-phase-portion case Ca (the first case portion) and the gas-phase-portion case Cb (the second case portion) can be joined to each other into an assembly (S5).

When the assembling of the liquid-phase-portion case Ca (the first case portion) and the gas-phase-portion case Cb (the second case portion) is complete, the enclosed space in the enclosing unit R is pressurized (S6). Subsequently, the door or the like of the enclosing unit R is opened, and the assembly is taken out of the enclosing unit R (S7). In S6, it is preferable to increase the pressure to, for example, the atmospheric pressure but is only necessary to increase the pressure to a level at which the door of the enclosing unit R can be opened. Thus, a series of welding steps ends, establishing a state where the pressure in the air gap ($\alpha$) produced between the sealing part Q1 and the fixing parts Q2 and Q3 of the assembly is negative to the atmospheric pressure. Note that S1 and S3 may be modified such that the gas-phase-portion case Cb is set in S1 and the liquid-phase-portion case Ca is set on the membrane member M in S3. Furthermore, S6 may be omitted.

Now, a method in which heating by the heating unit 13 is performed will be described with reference to the flow chart illustrated in FIG. 15. The liquid-phase-portion case Ca is positioned with respect to the jig 12 and is secured to the jig 12 (S1). Subsequently, the membrane member M is set on the secured liquid-phase-portion case Ca (S2). Then, the gas-phase-portion case Cb is set on the membrane member M (S3), whereby the liquid-phase-portion case Ca (the first case portion) and the gas-phase-portion case Cb (the second case portion) are mated to each other with the membrane member M interposed in between.

Subsequently, a hermetically enclosed space is produced in the enclosing unit R, and the heating unit 13 is activated, whereby the enclosed space is heated (S4). With the heating, the enclosed space is depressurized. In the depressurized state, the ultrasonic welding apparatus 11 is activated to press the horn 11a against the liquid-phase-portion case Ca (the first case portion) and the gas-phase-portion Cb (the second case portion), whereby the fixing parts Q2 and Q3 are pressed against each other and fixed (welded) to each other by the effect of the ultrasonic wave. Furthermore, pressing the horn 11a cases the sealing part Q1 to compress the membrane member M, whereby sealing is achieved. Thus, the liquid-phase-portion case Ca (the first case portion) and the gas-phase-portion case Cb (the second case portion) can be joined to each other into an assembly (S5).

When the assembling of the liquid-phase-portion case Ca (the first case portion) and the gas-phase-portion case Cb (the second case portion) is complete, the enclosed space in the enclosing unit R is cooled (S6). Subsequently, the door or the like of the enclosing unit R is opened, and the assembly is taken out of the enclosing unit R (S7). In S6, it is preferable to cool the enclosed space to, for example, the room temperature (the temperature outside the enclosing unit R) but is only necessary to cool the enclosed space to a level at which the assembly can be held by the hand when taken out of the enclosing unit R. Thus, a series of welding steps ends, establishing a state where the pressure in the air gap ($\alpha$) produced between the sealing part Q1 and the fixing parts Q2 and Q3 of the assembly is negative to the atmospheric pressure. Note that S1 and S3 may be modified such that the gas-phase-portion case Cb is set in S1 and the liquid-phase-portion case Ca is set on the membrane member M in S3. Furthermore, S6 may be omitted.

The pressure detector 10 as a medical device manufactured as above is heated at a temperature lower than or equal to the transition point or softening point of glass and is then cooled. Thus, an annealing process for removing the internal (residual) stress in the resin is performed. After the annealing process, autoclave sterilization is performed in which the pressure detector 10 is heated in saturated vapor for sterilization. Autoclave sterilization is performed in a high-pressure environment created by raising the boiling point so that the environment can have some moisture even at high temperatures. Subsequently, a drying process is performed. Thus, the pressure detector 10 as a medical device that has been wetted in autoclave sterilization is dried.

According to the present embodiment, when the fixing (welding) at the fixing parts Q2 and Q3 and the sealing by the sealing part Q1 are performed to assemble the liquid-phase-portion case Ca (the first case portion) and the gas-phase-portion case Cb (the second case portion) together, the air gap ($\alpha$) produced between the sealing part Q1 and the fixing parts Q2 and Q3 is depressurized or heated. Therefore, if the assembly including the liquid-phase-portion case Ca (the first case portion) and the gas-phase-portion case Cb (the second case portion) is subjected to annealing, autoclave sterilization, or a high-temperature environment of use, the occurrence of excessive pressure increase in the air gap ($\alpha$) produced between the sealing part Q1 and the fixing parts Q2 and Q3 can be suppressed. Consequently, improvements in quality and reliability can be achieved.

Furthermore, the liquid-phase-portion case Ca (the first case portion) and the gas-phase-portion case Cb (the second case portion) that are mated to each other with the membrane member M (the elastic membrane) interposed in between are secured to the jig 12; the fixing (welding) at the fixing parts Q2 and Q3 and the sealing by the sealing part Q1 are performed to assemble the liquid-phase-portion case Ca (the first case portion) and the gas-phase-portion case Cb (the second case portion) together; at least the liquid-phase-portion case Ca (the first case portion) and the gas-phase-portion case Cb (the second case portion) that are secured to the jig 12 are hermetically enclosed in an enclosed space; and the enclosed space is depressurized or heated. Therefore, depressurization or heating of the air gap ($\alpha$) can be achieved efficiently. In particular, according to the present embodiment, after the enclosed space is depressurized or heated, the enclosed space is pressurized or cooled. Therefore, the finished product can be taken out after the environment is stabilized. Hence, an improvement in quality can be achieved.

Furthermore, the case C according to the present embodiment is connectable to the flow route for liquid; the first housing space serves as the liquid-phase portion S1 to be supplied with the liquid in the flow route; the second housing space serves as the gas-phase portion S2 to be supplied with gas; the elastic membrane is the membrane member M with which the liquid-phase portion and the gas-phase portion are separated from each other and that is displaceable in accordance with the pressure of the liquid supplied into the liquid-phase portion; and the medical device serves as the pressure detector 10 that detects the pressure of the liquid in the flow route by detecting the pressure in the gas-phase portion S2. Therefore, the occurrence of excessive pressure increase in the air gap ($\alpha$) produced between the sealing part Q1 and the fixing parts Q2 and Q3 is suppressed. Consequently, the quality and reliability of the pressure detector 10 can be improved.

While an embodiment has been described above, the present invention is not limited thereto. For example, the enclosing unit R may provide a hermetically enclosed space that encloses the entirety of the ultrasonic welding apparatus 11 and the jig 12. Moreover, the entire atmosphere of the room where the assembling of the liquid-phase-portion case Ca (the first case portion) and the gas-phase-portion case Cb (the second case portion) is performed may be depressurized or heated. Furthermore, in the above embodiment, the liquid-phase-portion case Ca (the first case portion) and the gas-phase-portion case Cb (the second case portion) are welded to each other by melting the fixing parts Q2 and Q3 with an ultrasonic wave. As an alternative to ultrasonic welding, another fixing process (such as laser welding, or an assembling process of press-fitting or screwing) may be employed.

The pressure detector 10 according to the above embodiment is connected to a position of the venous blood circuit 2 that is between the dialyzer 3 and the air-trap chamber 5. Alternatively, the pressure detector 10 may be connected to another position of the blood circuit (for example, a position of the arterial blood circuit 1 that is between the distal end and the blood pump 4, or a position of the arterial blood circuit 1 that is between the blood pump 4 and the dialyzer 3). The blood circuit to which the present pressure detector 10 is to be connected may be of another type. For example, the blood circuit may be provided with the present pressure detector 10 instead of the air-trap chamber 5.

The liquid-phase-portion case Ca is not limited to the one having two ports serving as the inlet port C1 and the outlet port C2 as in the above embodiment. For example, the liquid-phase-portion case Ca may be the one having a single port C4 as illustrated in FIGS. 16 and 17, or the one having five ports (C5 to C9) as illustrated in FIGS. 18 and 19. In the example illustrated in FIGS. 18 and 19, the number of ports to be provided to the liquid-phase-portion case Ca is not limited to five and may be four, six, or seven or more.

The above embodiment concerns the pressure detector 10 provided to a blood circuit intended for dialysis treatment. Alternatively, the present invention may be applied to another medical device (such as a diaphragm pump) including a case obtained by mating a first case portion and a second case portion to each other, the case having a housing space inside; an elastic membrane as an elastic member attached to the case and with which a first housing space covered by the first case portion and a second housing space covered by the second case portion are separated from each other; fixing parts provided at the respective peripheries of the first case portion and the second case portion and at which the first case portion and the second case portion that are mated to each other are fixed to each other; holding surfaces provided at the respective peripheries of the first case portion and the second case portion and between which the peripheral edge of the elastic membrane is held; and a sealing part provided at the periphery of the first case portion or the second case portion on the inner side with respect to the fixing parts and that seals the entirety of the peripheral edge of the elastic membrane held between the holding surfaces.

For example, if the one illustrated in FIGS. 16 and 17 is used as a diaphragm pump, the following configuration may be employed: an air pump 20 and a pressure sensor 21 are connected to the connection port C3, the port C4 is connected to the flow route for liquid, and a valve Va and a valve Vb are provided to the upstream side and the downstream side, respectively, of the flow route, whereby the diaphragm pump is controlled. In such a case, when the air pump 20 is activated with the valve Va open and the valve Vb closed, the membrane member M is attracted toward the wall of the gas-phase-portion case Cb (the second case portion). Thus, the liquid can be introduced into the liquid-phase-portion case Ca. On the other hand, when the air pump 20 is activated reversely with the valve Va closed and the valve Vb open, the membrane member M is attracted toward the wall of the liquid-phase-portion case Ca (the first case portion). Thus, the liquid in the liquid-phase-portion case Ca can be discharged. With the repetition of the above activation of the air pump 20 and operation of the valves Va and Vb, the medical device can function as a diaphragm pump. The above drawings illustrate a case where the pressure sensor 21 is capable of detecting the attraction of the membrane member M to the wall of the liquid-phase-portion case Ca (the first case portion) or the gas-phase-portion case Cb (the second case portion). Alternatively, such a pressure sensor 21 may be omitted.

As another example, if the one illustrated in FIGS. 18 and 19 is used as a diaphragm pump, the following configuration may be employed: an air pump 20 and a pressure sensor 21 are connected to the connection port C3, the ports C5 to C9 are connected to respective flow routes for liquid, and valves V1 to V5 are provided to the respective flow routes, whereby the diaphragm pump is controlled. In such a case, when the air pump 20 is activated with the valve V1 open and the other valves V2 to V5 closed, the membrane member M is attracted toward the wall of the gas-phase-portion case Cb (the second case portion). Thus, the liquid can be introduced into the liquid-phase-portion case Ca. On the other hand, when the air pump 20 is activated reversely with the valve V1 closed and the other valves V2 to V5 open, the membrane member M is attracted toward the wall of the liquid-phase-portion case Ca (the first case portion). Thus, the liquid in the liquid-phase-portion case Ca can be discharged. With the repetition of the above activation of the air pump 20 and operation of the valves V1 to V5, the medical device can function as a diaphragm pump. The above drawings illustrate a case where the pressure sensor 21 is capable of detecting the attraction of the membrane member M to the wall of the liquid-phase-portion case Ca (the first case portion) or the gas-phase-portion case Cb (the second case portion). Alternatively, such a pressure sensor 21 may be omitted.

The present invention is applicable to any method and apparatus of manufacturing a medical device in any other mode or for any other use in which when fixing at fixing parts and sealing by a sealing part are performed to assemble a first case portion and a second case portion together, an air gap produced between the sealing part and the fixing parts is depressurized or heated.

REFERENCE SIGN LIST 1 arterial blood circuit
2 venous blood circuit
3 dialyzer (blood purifier)
4 blood pump
5 air-trap chamber
6 dialysis device
7 storage unit
8 air-trap chamber
9 clamp unit
10 pressure detector
11 ultrasonic welding apparatus
12 jig
13 depressurizing unit (heating unit)
L1 dialysate introduction line
L2 dialysate drain line
L3 physiological-saline supply line
C case
Ca liquid-phase-portion case (first case portion)
Ca1 inlet opening
Ca2 outlet opening
Cb gas-phase-portion case (second case portion)
Cb1 opening
Cb2 rib
Cb3 ridge
Cb4 recess
C1 inlet port
C1a flow-route portion
C1b connecting portion
C2 outlet port
C2a flow-route portion
C2b connecting portion
C3 connection port
M membrane member (elastic membrane)
Ma periphery
P pressure detection sensor (pressure-detecting unit)
S1 liquid-phase portion (first housing space)
S2 gas-phase portion (second housing space)
K pipe
Q1 sealing part
Q2, Q3 fixing part
m1, m2 holding surface
α air gap
R enclosing unit

The invention claimed is:

1. A method of manufacturing a medical device comprising:
creating a case by mating a first case portion and a second case portion to each other, the case having a housing space inside;
forming an inlet port and an outlet port that are integrally molded within the first case portion;
forming a connection port within the second case portion;
attaching an elastic membrane as an elastic member to the case and with which a first housing space covered by the first case portion and a second housing space covered by the second case portion are separated from each other, wherein the elastic membrane separates a liquid-phase portion and a gas-phase portion within the medical device;
providing fixing parts at respective peripheries of the first case portion and the second case portion and at which the first case portion and the second case portion that are mated to each other are fixed to each other;
providing holding surfaces at the respective peripheries of the first case portion and the second case portion and between which a peripheral edge of the elastic membrane is held; and
providing a sealing part at the periphery of the first case portion or the second case portion on an inner side with respect to the fixing parts and that seals an entirety of the peripheral edge of the elastic membrane held between the holding surfaces,
sealing the first case portion and the second case portion together with the sealing part to assemble the first case portion and the second case portion together;
fixing with the fixing parts the first case portion and the second case portion together;
producing an air gap between the sealing part and the fixing parts;
depressurizing or heating the air gap of the sealing part and the fixing parts before the step of fixing with the fixing parts the first case portion and the second case portion together, wherein the air gap is gas-tight; and
annealing or autoclave sterilizing the medical device after the air gap is depressurized or heated; and
wherein the sealing part is a ridge projecting from the holding surfaces, and a portion of the air gap is located between the ridge and the elastic membrane.

2. The method of manufacturing a medical device according to claim 1, wherein the first case portion and the second case portion that are mated to each other with the elastic membrane interposed in between are secured to a jig; the fixing at the fixing parts and the sealing by the sealing part are performed to assemble the first case portion and the second case portion together; at least the first case portion and the second case portion that are secured to the jig are hermetically enclosed in an enclosed space; and the enclosed space is depressurized or heated.

3. The method of manufacturing a medical device according to claim 1, wherein the case is connectable to a flow route for liquid; the first housing space serves as the liquid-phase portion to be supplied with the liquid in the flow route; the second housing space serves as the gas-phase portion to be supplied with gas; the elastic membrane is a membrane member with which the liquid-phase portion and the gas-phase portion are separated from each other and that is displaceable in accordance with a pressure of the liquid supplied into the liquid-phase portion; and the medical device serves as a pressure detector that detects the pressure of the liquid in the flow route by detecting a pressure in the gas-phase portion.

4. The method of manufacturing a medical device according to claim 3, further comprising a plurality of ribs in a recess of the gas-phase portion.

5. The method of manufacturing a medical device according to claim 1, further comprising fixing at the fixing parts and sealing by the sealing part to assemble the first case portion and the second case portion together forming the air gap as an enclosed space;
   depressurizing the enclosed space to establish a state where a pressure in the enclosed space is negative compared to atmospheric pressure after the first case portion and the second case portion are assembled; or
   heating the first case portion and the second case portion when fixing the fixing parts, sealing by the sealing parts, and then cooling to establish a state where the pressure is negative within the enclosed space compared to the atmospheric pressure.

6. The method of manufacturing a medical device according to claim 1, wherein a height direction dimension of the peripheral edge of the elastic membrane in a state before the first case portion and the second case portion are fixed or assembled, is smaller than a height direction dimension of the air gap.

7. The method of manufacturing a medical device according to claim 1, further comprising compressing the elastic membrane with the ridge when the first case portion is connected to the second case portion.

8. The method of manufacturing a medical device according to claim 1, further comprising:
   forming the air gap during a process of bringing the first case portion and the second case portion into contact with each other and the air gap consists of a space between the sealing part and the fixing part, and
   securing the first case portion and the second case portion to each other and to a jig with the elastic membrane interposed in between; and
   assembling the first case portion and the second case portion together by fixing at the fixing parts and sealing by the sealing part, wherein at least the first case portion and the second case portion that are secured to the jig are hermetically enclosed in an enclosed space.

9. The method of manufacturing a medical device according to claim 8, wherein the enclosed space is pressurized or cooled after the enclosed space is depressurized or heated.

10. A system comprising:
    a medical device comprising:
       a case obtained by mating a first case portion and a second case portion to each other, the case having a housing space inside;
       an elastic membrane as an elastic member attached to the case and with which a first housing space covered by the first case portion and a second housing space covered by the second case portion are separated from each other, wherein the elastic membrane separates a liquid-phase portion and a gas-phase portion within the medical device;
       fixing parts provided at respective peripheries of the first case portion and the second case portion and at which the first case portion and the second case portion that are mated to each other are fixed to each other;
       holding surfaces provided at the respective peripheries of the first case portion and the second case portion and between which a peripheral edge of the elastic membrane is held;
       an inlet port and an outlet port integrally molded within the first case portion and providing a flow route of liquid through the liquid-phase portion of the medical device;
       a connection port located within the second case portion and providing a flow route of gas through the gas-phase portion of the medical device; and
       a sealing part provided at the periphery of the first case portion or the second case portion on an inner side with respect to the fixing parts and that seals an entirety of the peripheral edge of the elastic membrane held between the holding surfaces,
    wherein the system further comprises a depressurizing unit or a heater, wherein when fixing at the fixing parts and sealing by the sealing part are performed to assemble the first case portion and the second case portion together, the depressurizing unit or the heater depressurizes or heats an air gap produced between the sealing part and the fixing parts so that the air gap is gas-tight, wherein the depressurizing unit or the heater depressurizes or heats the air gap before the first case portion and the second case portion are fixed by the fixing parts; and
    wherein annealing or autoclave sterilization is performed to the medical device after the air gap is depressurized by the depressurizing unit or heated by the heater; and
    wherein the sealing part is a ridge projecting from the holding surfaces, and a portion of the air gap is located between the ridge and the elastic membrane.

11. The system according to claim 10, further comprising:
    a jig to which the first case portion and the second case portion that are mated to each other with the elastic membrane interposed in between are secured; and
    an enclosing unit that hermetically encloses at least the first case portion and the second case portion in an enclosed space while the first case portion and the second case portion are secured to the jig,
    wherein when the fixing at the fixing parts and the sealing by the sealing part are performed to assemble the first case portion and the second case portion together, the depressurizing unit or the heater depressurizes or heats the hermetically enclosed space produced in the enclosing unit, and after the enclosed space is depressurized or heated the enclosed space is pressurized or cooled to maintain a negative pressure in the air gap.

12. The system according to claim 11, wherein the first case portion and the second case portion are in contact and sealed together forming the air gap and the air gap comprises a space between the sealing part and the fixing part.

13. The system according to claim 10, wherein the case is connectable to a flow route for liquid; the first housing space serves as the liquid-phase portion to be supplied with the liquid in the flow route; the second housing space serves as the gas-phase portion to be supplied with gas; the elastic membrane is a membrane member with which the liquid-phase portion and the gas-phase portion are separated from each other and that is displaceable in accordance with a pressure of the liquid supplied into the liquid-phase portion; and the medical device serves as a pressure detector that detects the pressure of the liquid in the flow route by detecting a pressure in the gas-phase portion.

14. The system according to claim 13, further comprising a plurality of ribs in a recess of the gas-phase portion.

15. The system according to claim 10, wherein the first case portion and the second case portion are sealed together forming the air gap as an enclosed space by the fixing parts and the sealing parts being sealed together;

wherein the enclosed space is depressurized to establish a state where a pressure therein is negative to an atmosphere pressure after assembly; or wherein the fixing parts and the sealing part are fixed together so that the first case portion and the second case portion are assembled together, and the enclosed space is negative to the atmospheric pressure by heating and cooling the assembly.

16. The system according to claim 10, wherein a height direction dimension of the peripheral edge of the elastic membrane in a state before the first case portion and the second case portion are fixed or assembled, is smaller than a height direction dimension of the air gap.

17. The system according to claim 10, wherein the ridge extends into the elastic membrane and compresses the elastic membrane when the first case portion is connected to the second case portion.

18. The system according to claim 10, wherein the elastic membrane is impermeable so that the liquid-phase and the gas-phase are prevented from passing through the elastic membrane.

* * * * *